(12) United States Patent
Achen et al.

(10) Patent No.: US 7,534,572 B2
(45) Date of Patent: May 19, 2009

(54) METHODS FOR TREATING NEOPLASTIC DISEASE CHARACTERIZED BY VASCULAR ENDOTHELIAL GROWTH FACTOR D EXPRESSION, FOR SCREENING FOR NEOPLASTIC DISEASE OR METASTATIC RISK, AND FOR MAINTAINING VASCULARIZATION OF TISSUE

(75) Inventors: Marc Achen, Victoria (AU); Steven Stacker, Victoria (AU)

(73) Assignee: Vegenics Limited, Toorak (AU)

( * ) Notice: Subject to any disclaimer, the term of this patent is extended or adjusted under 35 U.S.C. 154(b) by 177 days.

(21) Appl. No.: 10/627,631

(22) Filed: Jul. 28, 2003

(65) Prior Publication Data

US 2005/0202015 A1 Sep. 15, 2005

Related U.S. Application Data

(63) Continuation of application No. 09/956,095, filed on Sep. 20, 2001, now abandoned, which is a continuation-in-part of application No. 09/796,714, filed on Mar. 2, 2001, now abandoned.

(60) Provisional application No. 60/234,196, filed on Sep. 20, 2000, provisional application No. 60/186,361, filed on Mar. 2, 2000.

(51) Int. Cl.
  *G01N 33/53* (2006.01)
  *G01N 33/559* (2006.01)
  *G01N 33/561* (2006.01)
  *G01N 33/574* (2006.01)
  *G01N 33/577* (2006.01)
  *C12P 21/08* (2006.01)

(52) U.S. Cl. .................... 435/7.1; 435/7.23; 530/387.1; 530/388.1; 530/388.23; 530/391.3

(58) Field of Classification Search .................. 435/7.1; 530/391.1, 393.1, 388.24
See application file for complete search history.

(56) References Cited

U.S. PATENT DOCUMENTS 6,235,713 B1  5/2001  Achen et al.
6,730,489 B1 *  5/2004  Achen et al. ................. 435/7.1

FOREIGN PATENT DOCUMENTS

| EP | 0935001 | 8/1999 |
| WO | WO98/07832 | 2/1998 |
| WO | WO 99/33485 | * 7/1999 |
| WO | WO 00/37025 | 6/2000 |
| WO | WO 00/77190 | 12/2000 |

OTHER PUBLICATIONS

Achen et al, Eur J Biochem 267: 2505-2515, May 2000.*
Barrios et al, J Molecular Recognition 17: 332-338, 2004.*
Kurebayashi et al, Jpn J Cancer Res 90: 977-981, Sep. 1999.*
Achen et al, Proc. Nat. Acad. Sci USA 95: 548-553, Jan. 1998.*
Valtola et al, American J of Pathology 154(5): 1381-1390, May 1999.*
Tsurusaki et al, Br J Cancer 80(1-2):309-13, Apr. 1999.*
Salven et al, Am J Pathol 153(1):103-8, Jul. 1998.*
Stryer et al, 1988, in Biochemistry, Third Edition, W. H. Freeman and Company/New York, pp. 31-33.*
Kuby et al., 1994, Immunology, second edition, pp. 85-96.*
Abaza et al, J of Protein Chemistry 11(5): 433-444, 1992.*
Filip Farnebo, et al., "Restricted Expression Pattern of *vegf-d* in the Adult and Fetal Mouse: High Expression in the Embryonic Lung" Biochemical and Bio physical Research Communications, vol. 257, pp. 891-894 (1999).
Marc G. Achen, et al., "Vascular endothelial growth factor D (VEGF-D) is a ligand for the gyrosine kinases VEGF receptor 2 (Flk1) and VEGF receptor 3 (Flt4)" Proc. National Acad. Of Science, vol. 95, pp. 548-553, Jan. 1998.
European Search Report dated Apr. 7, 2003.
International Search Report dated Jun. 5, 2001.
Achen, Marc G. et al., "Localization of Vascular Endothelial Growth Factor-D in Malignant Melanoma Suggests a Role in Tumour Angiogenesis," *Journal of Pathology*, vol. 193, pp. 147-154 (2001).
O-charoenrat, Pornchai et al., "Vascular Endothelial Growth Factor Family Members are Differentially Regulated by *c-erb* Signaling in Head and Neck Squamous Carcinoma Cells," *Clinical & Experimental Metastasis*, vol. 18, pp. 155-161 (2000).
Stacker, Steven A et al., "VEGF-D Promotes the Metastatic Spread of Tumor Cells via the Lymphatics," *Nature Medicine*, vol. 7, No. 2, pp. 186-191 (2001).
Achen et al., Proc. Nat. Acad. Sci USA 95:548-553, Jan. 1998.
Valtola et al., American J. of Pathology 154(5): 1381-1390, May 1999.
Tsurusaki et al., Br. J. Cancer 80(1-2): 309-13, Apr. 1999.
Salven et al., Am. J. Pathol 153(1): 103-8, Jul. 1998.
Stryer et al., 1988, Biochemistry, Third Edition, W.H. Freeman and Company, New York, pp. 31-33.
Abaza et al., J. of Protein Chemistry 11(5): 433-444, 1992.

* cited by examiner

*Primary Examiner*—Phuong Huynh
(74) *Attorney, Agent, or Firm*—Marshall, Gerstein & Borun LLP

(57) ABSTRACT

A method for treating and alleviating disease characterized by the expression of VEGF-D involving screening to find an organism with tumor cells expressing VEGF-D and administering an effective amount of a VEGF-D antagonist; a method for screening for neoplastic diseas, where detection of VEGF-D on or in a sample such as tumor cells, blood vessel endothelial cells or lymph vessel endothelial cells indicates neoplastic disease; a method for promoting and maintaining vascularization of normal tissue in an organism involving administering a vascularization promoting amount of VEGF-D or a fragment or analog thereof to the organism; a method for screening tumors for metastatic risk involving detecting expression of VEFG-D by a tumor which indicates metastatic risk; and a method of detecting micro-metastasis of neoplastic disease involving detection of VEGF-D on or in a tissue sample which indicates metastasis of a neoplastic disease.

11 Claims, 21 Drawing Sheets

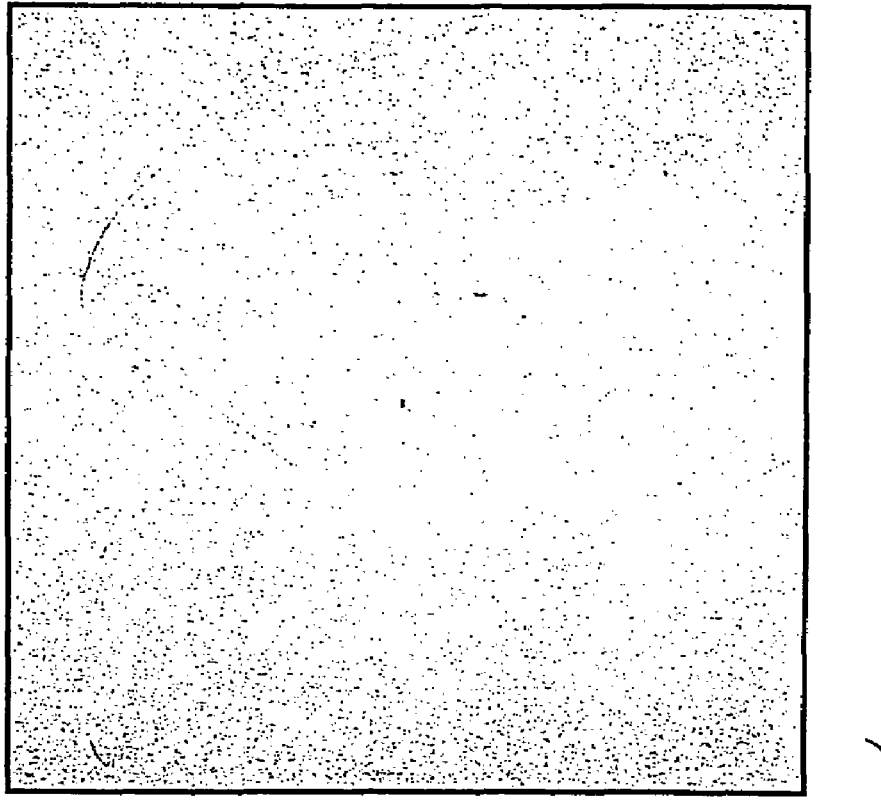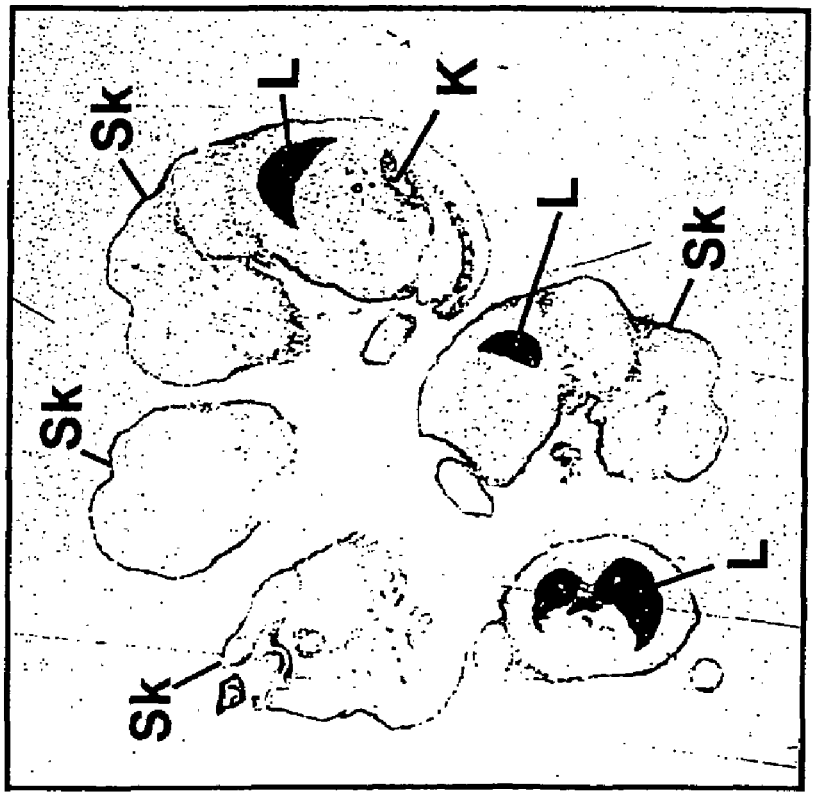
Fig. 3

SEQUENCE LISTING

```
<160> NUMBER OF SEQ ID NOS: 4

<210> SEQ ID NO 1
<211> LENGTH: 2029
<212> TYPE: DNA
<213> ORGANISM: Homo sapiens
<220> FEATURE:
<221> NAME/KEY: CDS
<222> LOCATION: (411)..(1472)
<223> OTHER INFORMATION:

<400> SEQUENCE: 1
gttgggttcc agctttctgt agctgtaagc attggtggcc acaccacctc cttacaaagc        60
aactagaacc tgcggcatac attggagaga ttttttttaat tttctggaca tgaagtaaat      120
ttagagtgct ttctaatttc aggtagaaga catgtccacc ttctgattat ttttggagaa      180
cattttgatt tttttcatct ctctctcccc accccctaaga ttgtgcaaaa aaagcgtacc      240
ttgcctaatt gaaataattt cattggattt tgatcagaac tgattatttg gttttctgtg      300
tgaagttttg aggtttcaaa ctttccttct ggagaatgcc ttttgaaaca attttctcta      360
gctgcctgat gtcaactgct tagtaatcag tggatattga aatattcaaa atg tac         416
                                                        Met Tyr
                                                          1 aga gag tgg gta gtg gtg aat gtt ttc atg atg ttg tac gtc cag ctg         464
Arg Glu Trp Val Val Val Asn Val Phe Met Met Leu Tyr Val Gln Leu
          5                  10                  15 gtg cag ggc tcc agt aat gaa cat gga cca gtg aag cga tca tct cag         512
Val Gln Gly Ser Ser Asn Glu His Gly Pro Val Lys Arg Ser Ser Gln
     20                  25                  30 tcc aca ttg gaa cga tct gaa cag cag atc agg gct gct tct agt ttg         560
Ser Thr Leu Glu Arg Ser Glu Gln Gln Ile Arg Ala Ala Ser Ser Leu
 35                  40                  45                  50 gag gaa cta ctt cga att act cac tct gag gac tgg aag ctg tgg aga         608
Glu Glu Leu Leu Arg Ile Thr His Ser Glu Asp Trp Lys Leu Trp Arg
                 55                  60                  65 tgc agg ctg agg ctc aaa agt ttt acc agt atg gac tct cgc tca gca         656
Cys Arg Leu Arg Leu Lys Ser Phe Thr Ser Met Asp Ser Arg Ser Ala
             70                  75                  80 tcc cat cgg tcc act agg ttt gcg gca act ttc tat gac att gaa aca         704
Ser His Arg Ser Thr Arg Phe Ala Ala Thr Phe Tyr Asp Ile Glu Thr
```

-continued

|  | 85 |  |  | 90 |  |  | 95 |  |  |  |  |  |  |
|---|---|---|---|---|---|---|---|---|---|---|---|---|---|
| cta | aaa | gtt | ata | gat | gaa | gaa | tgg | caa | aga | act | cag | tgc | agc | cct | aga | 752 |
| Leu | Lys | Val | Ile | Asp | Glu | Glu | Trp | Gln | Arg | Thr | Gln | Cys | Ser | Pro | Arg |  |
|  | 100 |  |  |  | 105 |  |  |  | 110 |  |  |  |  |  |  |  |

```
cta aaa gtt ata gat gaa gaa tgg caa aga act cag tgc agc cct aga    752
Leu Lys Val Ile Asp Glu Glu Trp Gln Arg Thr Gln Cys Ser Pro Arg
    100                 105                 110 gaa acg tgc gtg gag gtg gcc agt gag ctg ggg aag agt acc aac aca    800
Glu Thr Cys Val Glu Val Ala Ser Glu Leu Gly Lys Ser Thr Asn Thr
115                 120                 125                 130 ttc ttc aag ccc cct tgt gtg aac gtg ttc cga tgt ggt ggc tgt tgc    848
Phe Phe Lys Pro Pro Cys Val Asn Val Phe Arg Cys Gly Gly Cys Cys
                135                 140                 145 aat gaa gag agc ctt atc tgt atg aac acc agc acc tcg tac att tcc    896
Asn Glu Glu Ser Leu Ile Cys Met Asn Thr Ser Thr Ser Tyr Ile Ser
            150                 155                 160 aaa cag ctc ttt gag ata tca gtg cct ttg aca tca gta cct gaa tta    944
Lys Gln Leu Phe Glu Ile Ser Val Pro Leu Thr Ser Val Pro Glu Leu
        165                 170                 175 gtg cct gtt aaa gtt gcc aat cat aca ggt tgt aag tgc ttg cca aca    992
Val Pro Val Lys Val Ala Asn His Thr Gly Cys Lys Cys Leu Pro Thr
    180                 185                 190 gcc ccc cgc cat cca tac tca att atc aga aga tcc atc cag atc cct   1040
Ala Pro Arg His Pro Tyr Ser Ile Ile Arg Arg Ser Ile Gln Ile Pro
195                 200                 205                 210 gaa gaa gat cgc tgt tcc cat tcc aag aaa ctc tgt cct att gac atg   1088
Glu Glu Asp Arg Cys Ser His Ser Lys Lys Leu Cys Pro Ile Asp Met
                215                 220                 225 cta tgg gat agc aac aaa tgt aaa tgt gtt ttg cag gag gaa aat cca   1136
Leu Trp Asp Ser Asn Lys Cys Lys Cys Val Leu Gln Glu Glu Asn Pro
            230                 235                 240 ctt gct gga aca gaa gac cac tct cat ctc cag gaa cca gct ctc tgt   1184
Leu Ala Gly Thr Glu Asp His Ser His Leu Gln Glu Pro Ala Leu Cys
        245                 250                 255 ggg cca cac atg atg ttt gac gaa gat cgt tgc gag tgt gtc tgt aaa   1232
Gly Pro His Met Met Phe Asp Glu Asp Arg Cys Glu Cys Val Cys Lys
    260                 265                 270 aca cca tgt ccc aaa gat cta atc cag cac ccc aaa aac tgc agt tgc   1280
Thr Pro Cys Pro Lys Asp Leu Ile Gln His Pro Lys Asn Cys Ser Cys
275                 280                 285                 290 ttt gag tgc aaa gaa agt ctg gag acc tgc tgc cag aag cac aag cta   1328
Phe Glu Cys Lys Glu Ser Leu Glu Thr Cys Cys Gln Lys His Lys Leu
                295                 300                 305 ttt cac cca gac acc tgc agc tgt gag gac aga tgc ccc ttt cat acc   1376
Phe His Pro Asp Thr Cys Ser Cys Glu Asp Arg Cys Pro Phe His Thr
            310                 315                 320 aga cca tgt gca agt ggc aaa aca gca tgt gca aag cat tgc cgc ttt   1424
Arg Pro Cys Ala Ser Gly Lys Thr Ala Cys Ala Lys His Cys Arg Phe
        325                 330                 335 cca aag gag aaa agg gct gcc cag ggg ccc cac agc cga aag aat cct   1472
Pro Lys Glu Lys Arg Ala Ala Gln Gly Pro His Ser Arg Lys Asn Pro
    340                 345                 350 tgattcagcg ttccaagttc cccatccctg tcatttttaa cagcatgctg ctttgccaag   1532
ttgctgtcac tgtttttttc ccaggtgtta aaaaaaaaat ccattttaca cagcaccaca   1592
gtgaatccag accaaccttc cattcacacc agctaaggag tccctggttc attgatggat   1652
gtgttctagc tgcagatgcc tctgcgcacc aaggaatgga gaggagggga cccatgtaat   1712 cctttttgttt agttttgttt tgttttttg gtgaatgaga aaggtgtgct ggtcatggaa   1772
tggcaggtgt catatgactg attactcaga gcagatgagg aaaactgtag tctctgagtc   1832
ctttgctaat cgcaactctt gtgaattatt ctgattcttt tttatgcaga atttgattcg   1892
```

-continued

```
tatgatcagt actgactttc tgattactgt ccagcttata gtcttccagt ttaatgaact    1952
accatctgat gtttcatatt taagtgtatt taaagaaaat aaacaccatt attcaagcca    2012
aaaaaaaaaa aaaaaaa                                                   2029
```

<210> SEQ ID NO 2
<211> LENGTH: 354
<212> TYPE: PRT
<213> ORGANISM: Homo sapiens

<400> SEQUENCE: 2

```
Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Gly Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
```

Asn Pro

<210> SEQ ID NO 3
<211> LENGTH: 109
<212> TYPE: PRT
<213> ORGANISM: Homo sapiens

<400> SEQUENCE: 3

Phe Tyr Asp Ile Glu Thr Leu Lys Val Ile Asp Glu Glu Trp Gln Arg
1               5                   10                  15

Thr Gln Cys Ser Pro Arg Glu Thr Cys Val Glu Val Ala Ser Glu Leu
            20                  25                  30

Gly Lys Ser Thr Asn Thr Phe Phe Lys Pro Pro Cys Val Asn Val Phe
        35                  40                  45

Arg Cys Gly Gly Cys Cys Asn Glu Glu Ser Leu Ile Cys Met Asn Thr
    50                  55                  60

Ser Thr Ser Tyr Ile Ser Lys Gln Leu Phe Glu Ile Ser Val Pro Leu
65                  70                  75                  80

Thr Ser Val Pro Glu Leu Val Pro Val Lys Val Ala Asn His Thr Gly
                85                  90                  95

Cys Lys Cys Leu Pro Thr Ala Pro Arg His Pro Tyr Ser
            100                 105

<210> SEQ ID NO 4
<211> LENGTH: 1325
<212> TYPE: DNA
<213> ORGANISM: Murinae gen. sp.

<400> SEQUENCE: 4
ggagaatgcc ttttgcaaca cttttcagta gctgcctgga acaactgct tagtcatcgg      60
tagacattta aaatattcaa aatgtatgga gaatggggaa tggggaatat cctcatgatg    120
ttccatgtgt acttggtgca gggcttcagg agcgaacatg accagtgaa ggattttct     180
tttgagcgat catcccggtc catgttggaa cgatctgaac aacagatccg agcagcttct    240
agtttggagg agttgctgca aatcgcgcac tctgaggact ggaagctgtg gcgatgccgg    300
ttgaagctca aaagtcttgc cagtatggac tcacgctcag catcccatcg ctccaccaga    360
tttgcggcaa cttctatga cactgaaaca ctaaaagtta tagatgaaga atggcagagg     420
acccaatgca gccctagaga gacatgcgta gaagtcgcca gtgagctggg gaagacaacc    480
aacacattct tcaagccccc ctgtgtaaat gtcttccggt gtggaggctg ctgcaacgaa    540
gagggtgtga tgtgtatgaa cacaagcacc tcctacatct ccaaacagct ctttgagata    600
tcagtgcctc tgacatcagt gcccgagtta gtgcctgtta aaattgccaa ccatacgggt    660
tgtaagtgct tgcccacggg ccccgccat cttactcaa ttatcagaag atccattcag      720
accccagaag aagatgaatg tcctcattcc aagaaactct gtcctattga catgctgtgg    780
gataacacca atgtaaatg tgttttgcaa gacgagactc cactgcctgg acagaaagac    840
cactcttacc tccaggaacc cactctctgt ggaccgcaca tgacgtttga tgaagatcgc    900
tgtgagtgcg tctgtaaagc accatgtccg ggagatctca ttcagcaccc ggaaaactgc    960
agttgctttg agtgcaaaga aagtctggag agctgctgcc aaaagcacaa gattttcac    1020
ccagacacct gcagctgtga ggacagatgt ccttttcaca ccagaacatg tgcaagtaga   1080
aagccagcct gtggaaagca ctggcgcttt ccaaaggaga caagggccca gggactctac   1140

```
agccaggaga acccttgatt caacttcctt tcaagtcccc ccatctctgt cattttaaac    1200
agctcactgc tttgtcaagt tgctgtcact gttgcccact accccttgaa catgtgcaaa    1260
cacagacaca cacacacaca cacacacaga gcaactagaa ttatgttttc taggtgctgc    1320
ctaag                                                                1325
```

METHODS FOR TREATING NEOPLASTIC DISEASE CHARACTERIZED BY VASCULAR ENDOTHELIAL GROWTH FACTOR D EXPRESSION, FOR SCREENING FOR NEOPLASTIC DISEASE OR METASTATIC RISK, AND FOR MAINTAINING VASCULARIZATION OF TISSUE

CROSS-REFERENCE TO RELATED APPLICATIONS

This application is a continuation of U.S. application Ser. No. 09/956,095, filed Sep. 20, 2001, now abandoned, which is a continuation-in-part of U.S. application Ser. No. 09/796,714 filed on Mar. 2, 2001, now abandoned and claims priority of U.S. Provisional Application No. 60/186,361, filed Mar. 2, 2000 and U.S. Provisional Application No. 60/234,196, filed Sep. 20, 2000.

BACKGROUND OF THE INVENTION

The invention relates to a method for treating and alleviating melanomas and various cancers, methods for screening for neoplastic diseases, and a method for promoting and maintaining vascularization of normal tissue.

The two major components of the mammalian vascular system are the endothelial and smooth muscle cells. The endothelial cells form the lining of the inner surface of all blood vessels and lymphatic vessels in the mammal. The formation of new blood vessels can occur by two different processes, vasculogenesis or angiogenesis (for review see Risau, W., *Nature* 386: 671-674, 1997). Vasculogenesis is characterized by the in situ differentiation of endothelial cell precursors to mature endothelial cells and association of these cells to form vessels, such as occurs in the formation of the primary vascular plexus in the early embryo. In contrast, angiogenesis, the formation of blood vessels by growth and branching of pre-existing vessels, is important in later embryogenesis and is responsible for the blood vessel growth which occurs in the adult. Angiogenesis is a physiologically complex process involving proliferation of endothelial cells, degradation of extracellular matrix, branching of vessels and subsequent cell adhesion events. In the adult, angiogenesis is tightly controlled and limited under normal circumstances to the female reproductive system. However angiogenesis can be switched on in response to tissue damage. Importantly solid tumors are able to induce angiogenesis in surrounding tissue, thus sustaining tumor growth and facilitating the formation of metastases (Folkman, J.,*Nature Med.* 1: 27-31, 1995). The molecular mechanisms underlying the complex angiogenic processes are far from being understood.

Angiogenesis is also involved in a number of pathologic conditions, where it plays a role or is involved directly in different sequelae of the disease. Some examples include neovascularization associated with various liver diseases, neovascular sequelae of diabetes, neovascular sequelae to hypertension, neovascularization in post-trauma, neovascularization due to head trauma, neovascularization in chronic liver infection (e.g. chronic hepatitis), neovascularization due to heat or cold trauma, dysfunction related to excess of hormone, creation of hemangiomas and restenosis following angioplasty.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor alpha (TGFα), and hepatocyte growth factor (HGF). See for example Folkman et al., *J. Biol. Chem.*, 267: 10931-10934, 1992 for a review.

It has been suggested that a particular family of endothelial cell-specific growth factors, the vascular endothelial growth factors (VEGFs), and their corresponding receptors are primarily responsible for stimulation of endothelial cell growth and differentiation, and for certain functions of the differentiated cells. These factors are members of the PDGF/VEGF family, and appear to act primarily via endothelial receptor tyrosine kinases (RTKs). The PDGF/VEGF family of growth factors belongs to the cystine-knot superfamily of growth factors, which also includes the neurotrophins and transforming growth factor-β.

Eight different proteins have been identified in the PDGF/VEGF family, namely two PDGFs (A and B), VEGF and five members that are closely related to VEGF. The five members closely related to VEGF are: VEGF-B, described in International Patent Application PCT/US96/02957 (WO 96/26736) and in U.S. Pat. Nos. 5,840,693 and 5,607,918 by Ludwig Institute for Cancer Research and The University of Helsinki; VEGF-C or VEGF2, described in Joukov et al., *EMBO J.*, 15: 290-298, 1996, Lee et al., *Proc. Natl. Acad. Sci. USA*, 93: 1988-1992, 1996, and U.S. Pat. Nos. 5,932,540 and 5,935,540 by Human Genome Sciences, Inc; VEGF-D, described in International Patent Application No. PCT/US97/14696 (WO 98/07832), and Achen et al., *Proc. Natl. Acad. Sci. USA*, 95: 548-553, 1998; the placenta growth factor (PlGF), described in Maglione et al., Proc. Natl. Acad. Sci. USA, 88: 9267-9271, 1991; and VEGF3, described in International Patent Application No. PCT/US95/07283 (WO 96/39421) by Human Genome Sciences, Inc. Each VEGF family member has between 30% and 45% amino acid sequence identity with VEGF. The VEGF family members share a VEGF homology domain which contains the six cysteine residues which form the cystine-knot motif. Functional characteristics of the VEGF family include varying degrees of mitogenicity for endothelial cells, induction of vascular permeability and angiogenic and lymphangiogenic properties.

Vascular endothelial growth factor (VEGF) is a homodimeric glycoprotein that has been isolated from several sources. Alterative mRNA splicing of a single VEGF gene gives rise to five isoforms of VEGF. VEGF shows highly specific mitogenic activity for endothelial cells. VEGF has important regulatory functions in the formation of new blood vessels during embryonic vasculogenesis and in angiogenesis during adult life (Carmeliet et al., *Nature*, 380: 435-439, 1996; Ferrara et al., *Nature*, 380: 439-442, 1996; reviewed in Ferrara and Davis-Smyth, *Endocrine Rev.*, 18: 4-25, 1997). The significance of the role played by VEGF has been demonstrated in studies showing that inactivation of a single VEGF allele results in embryonic lethality due to failed development of the vasculature (Carmeliet et al., *Nature*, 380: 435-439, 1996; Ferrara et al., *Nature*, 380: 439-442, 1996). The isolation and properties of VEGF have been reviewed; see Ferrara et al., *J. Cellular Biochem.*, 47: 211-218, 1991 and Connolly, J. *Cellular Biochem.*, 47: 219-223, 1991.

In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). VEGF is also chemotactic for certain hematopoetic cells. Recent literature indicates that VEGF blocks maturation of dendritic cells and thereby reduces the effectiveness of the immune response to tumors (many tumors secrete VEGF) (Gabrilovich et al., *Blood* 92: 4150-4166, 1998; Gabrilovich et al., *Clinical Cancer Research* 5: 2963-2970, 1999).

VEGF-B has similar angiogenic and other properties to those of VEGF, but is distributed and expressed in tissues differently from VEGF. In particular, VEGF-B is very strongly expressed in heart, and only weakly in lung, whereas the reverse is the case for VEGF. This suggests that VEGF and VEGF-B, despite the fact that they are co-expressed in many tissues, may have functional differences.

VEGF-B was isolated using a yeast two-hybrid interaction trap screening technique by screening for cellular proteins which might interact with cellular retinoic acid-binding protein type I (CRABP-I). Its isolation and characteristics are described in detail in PCT/US96/02957 (WO 96/26736), in U.S. Pat. Nos. 5,840,693 and 5,607,918 by Ludwig Institute for Cancer Research and The University of Helsinki and in Olofsson et al., *Proc. Natl. Acad. Sci. USA,* 93: 2576-2581, 1996.

VEGF-C was isolated from conditioned media of the PC-3 prostate adenocarcinoma cell line (CRL1435) by screening for ability of the medium to produce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., *EMBO J.,* 15: 290-298, 1996.

VEGF-D was isolated from a human breast cDNA library, commercially available from Clontech, by screening with an expressed sequence tag obtained from a human cDNA library designated "Soares Breast 3NbHBst" as a hybridization probe (Achen et al., *Proc. Natl. Acad. Sci. USA,* 95: 548-553, 1998). Its isolation and characteristics are described in detail in International Patent Application No. PCT/US97/14696 (WO98/07832) and in U.S. Pat. No. 6,235,713 to Achen, et al.

In PCT/US97/14696, the isolation of a biologically active fragment of VEGF-D, designated VEGF-DΔNΔC, is also described. This fragment consists of VEGF-D amino acid residues 93 to 201 linked to the affinity tag peptide FLAG®. The entire disclosure of the International Patent Application PCT/US97/14696 (WO 98/07832) is incorporated herein by reference.

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., *Proc. Natl. Acad. Sci. USA,* 88: 9267-9271, 1991. Presently its biological function is not well understood.

VEGF3 was isolated from a cDNA library derived from colon tissue. VEGF3 is stated to have about 36% identity and 66% similarity to VEGF. The method of isolation of the gene encoding VEGF3 is unclear and no characterization of the biological activity is disclosed.

Similarity between two proteins is determined by comparing the amino acid sequence and conserved amino acid substitutions of one of the proteins to the sequence of the second protein, whereas identity is determined without including the conserved amino acid substitutions.

A major function of the lymphatic system is to provide fluid return from tissues and to transport many extravascular substances back to the blood. In addition, during the process of maturation, lymphocytes leave the blood, migrate through lymphoid organs and other tissues, and enter the lymphatic vessels, and return to the blood through the thoracic duct. Specialized venules, high endothelial venules (HEVs), bind lymphocytes again and cause their extravasation into tissues. The lymphatic vessels, and especially the lymph nodes, thus play an important role in immunology and in the development of metastasis of different tumors. Unlike blood vessels, the embryonic origin of the lymphatic system is not as clear, and at least three different theories exist as to its origin. Lymphatic vessels are difficult to identify due to the absence of known specific markers available for them.

Lymphatic vessels are most commonly studied with the aid of lymphography. In lymphography, X-ray contrast medium is injected directly into a lymphatic vessel. The contrast medium gets distributed along the efferent drainage vessels of the lymphatic system and is collected in the lymph nodes. The contrast medium can stay for up to half a year in the lymph nodes, during which time X-ray analyses allow the follow-up of lymph node size and architecture. This diagnostic technique is especially important in cancer patients with metastases in the lymph nodes and in lymphatic malignancies, such as lymphoma. However, improved materials and methods for imaging lymphatic tissues are needed in the art.

As noted above, the PDGF/VEGF family members act primarily by binding to receptor tyrosine kinases. In general, receptor tyrosine kinases are glycoproteins, which consist of an extracellular domain capable of binding a specific growth factor(s), a transmembrane domain, which is usually a hydrophobic and alpha-helical portion of the protein, a juxtamembrane domain, which is where the receptor may be regulated by, e.g., protein phosphorylation, a tyrosine kinase domain, which is the enzymatic component of the receptor and a carboxy-terminal tail, which in many receptors is involved in recognition and binding of the substrates for the tyrosine kinase.

Five receptor tyrosine kinases with specificity for endothelial cells have been identified, namely VEGFR-1 (Flt-1), VEGFR-2 (KDR/Flk-1), VEGFR-3 (Flt4), Tie and Tek/Tie-2. These receptors differ in their ligand specificity and affinity. All of these have the intrinsic tyrosine kinase activity which is necessary for signal transduction.

The only receptor tyrosine kinases known to bind VEGFs are VEGFR-1, VEGFR-2 and VEGFR-3. VEGFR-1 and VEGFR-2 bind VEGF with high affinity, and VEGFR-1 also binds VEGF-B and PlGF. VEGF-C has been shown to be the ligand for VEGFR-3, and it also activates VEGFR-2 (Joukov et al., *The EMBO Journal,* 15: 290-298, 1996). VEGF-D binds to both VEGFR-2 and VEGFR-3 (Achen et al., *Proc. Natl. Acad. Sci. USA,* 95: 548-553, 1998). A ligand for Tek/Tie-2 has been described in International Patent Application No. PCT/US95/12935 (WO 96/11269) by Regeneron Pharmaceuticals, Inc. The ligand for Tie has not yet been identified.

A novel 130-135 kDa VEGF isoform specific receptor has been purified and cloned (Soker et al., *Cell,* 92: 735-745, 1998). This VEGF receptor was found to specifically bind the $VEGF_{165}$ isoform via the exon 7 encoded sequence, which shows weak affinity for heparin (Soker et al., *Cell,* 92: 735-745, 1998). Surprisingly, the receptor was shown to be identical to human neuropilin-1 (NP-1), a receptor involved in early stage neuromorphogenesis. PlGF-2 also appears to interact with NP-1 (Migdal et al., *J. Biol. Chem.,* 273: 22272-22278, 1998).

VEGFR-1, VEGFR-2 and VEGFR-3 are expressed differently by endothelial cells. Generally, both VEGFR-1 and VEGFR-2 are expressed in blood vessel endothelia (Oelrichs et al., *Oncogene*, 8: 11-18, 1992; Kaipainen et al., *J. Exp. Med.*, 178: 2077-2088, 1993; Dumont et al., *Dev. Dyn.*, 203: 80-92, 1995; Fong et al., *Dev. Dyn.*, 207: 1-10, 1996) and VEGFR-3 is mostly expressed in the lymphatic endothelium of adult tissues (Kaipainen et al., *Proc. Natl. Acad. Sci. USA*, 9: 3566-3570, 1995). VEGFR-3 is also expressed in the blood vasculature surrounding tumors.

Although VEGFR-1 is mainly expressed in endothelial cells during development, it can also be found in hematopoetic precursor cells during early stages of embryogenesis (Fong et al., *Nature*, 376: 66-70, 1995). In adults, monocytes and macrophages also express this receptor (Barleon et al., *Blood*, 87: 3336-3343, 1995). In embryos, VEGFR-1 is expressed by most, if not all, vessels (Breier et al., *Dev. Dyn.*, 204: 228-239, 1995; Fong et al., *Dev. Dyn.*, 207: 1-10, 1996).

The receptor VEGFR-3 is widely expressed on endothelial cells during early embryonic development but as embryogenesis proceeds becomes restricted to venous endothelium and then to the lymphatic endothelium (Kaipainen et al., *Cancer Res.*, 54: 6571-6577, 1994; Kaipainen et al., *Proc. Natl. Acad. Sci. USA*, 92: 3566-3570, 1995). VEGFR-3 is expressed on lymphatic endothelial cells in adult tissues. This receptor is essential for vascular development during embryogenesis.

The essential, specific role in vasculogenesis, angiogenesis and/or lymphangiogenesis of VEGFR-1, VEGFR-2, VEGFR-3, Tie and Tek/Tie-2 has been demonstrated by targeted mutations inactivating these receptors in mouse embryos. Disruption of the VEGFR genes results in aberrant development of the vasculature leading to embryonic lethality around midgestation.

Analysis of embryos carrying a completely inactivated VEGFR-1 gene suggests that this receptor is required for functional organization of the endothelium (Fong et al., *Nature*, 376: 66-70, 1995). However, deletion of the intracellular tyrosine kinase domain of VEGFR-1 generates viable mice with a normal vasculature (Hiratsuka et al., *Proc. Natl. Acad. Sci. USA*, 95: 9349-9354, 1998). The reasons underlying these differences remain to be explained but suggest that receptor signalling via the tyrosine kinase is not required for the proper function of VEGFR-1.

Analysis of homozygous mice with inactivated alleles of VEGFR-2 suggests that this receptor is required for endothelial cell proliferation, hematopoesis and vasculogenesis (Shalaby et al., *Nature*, 376: 62-66, 1995; Shalaby et al., *Cell*, 89: 981-990, 1997).

Targeted inactivation of both copies of the VEGFR-3 gene in mice resulted in defective blood vessel formation characterized by abnormally organized large vessels with defective lumens, leading to fluid accumulation in the pericardial cavity and cardiovascular failure at post-coital day 9.5 (Dumont et al., *Science*, 282: 946-949, 1998). On the basis of these findings it has been proposed that VEGFR-3 is required for the maturation of primary vascular networks into larger blood vessels. However, the role of VEGFR-3 in the development of the lymphatic vasculature could not be studied in these mice because the embryos died before the lymphatic system emerged. Nevertheless it is assumed that VEGFR-3 plays a role in development of the lymphatic vasculature and lymphangiogenesis given its specific expression in lymphatic endothelial cells during embryogenesis and adult life. This is supported by the finding that ectopic expression of VEGF-C, a ligand for VEGFR-3, in the skin of transgenic mice, resulted in lymphatic endothelial cell proliferation and vessel enlargement in the dermis (Makinen et al., *Nature Med*, 7:199-205, 2001). Furthermore this suggests that VEGF-C may have a primary function in lymphatic endothelium, and a secondary function in angiogenesis and permeability regulation which is shared with VEGF (Joukov et al., *EMBO J.*, 15: 290-298, 1996).

In addition, VEGF-like proteins have been identified which are encoded by four different strains of the orf virus. This is the first virus reported to encode a VEGF-like protein. The first two strains are NZ2 and NZ7, and are described in Lyttle et al., *J. Virol.*, 68: 84-92, 1994. A third is D1701 and is described in Meyer et al., *EMBO J.*, 18: 363-374, 1999. The fourth strain is NZ10 and is described in International Patent Application PCT/US99/25869. It was shown that these viral VEGF-like proteins bind to VEGFR-2 on the endothelium of the host (sheep/goat/human) and this binding is important for development of infection (Meyer et al., *EMBO J.*, 18: 363-374, 1999; Ogawa et al., *J. Biol. Chem.*, 273: 31273-31282, 1988; Wise et al., *Proc. Natl. Acad. Sci. (US)*, 96: 3071-3076, 1999; and International Patent Application PCT/US99/25869). These proteins show amino acid sequence similarity to VEGF and to each other.

The orf virus is a type of species of the parapoxvirus genus which causes a highly contagious pustular dermatitis in sheep and goats and is readily transmittable to humans. The pustular dermatitis induced by orf virus infection is characterized by dilation of blood vessels, swelling of the local area and marked proliferation of endothelial cells lining the blood vessels. These features are seen in all species infected by orf and can result in the formation of a tumor-like growth or nodule due to viral replication in epidermal cells. Generally orf virus infections resolve in a few weeks, but severe infections that fail to resolve without surgical intervention are seen in immune impaired individuals.

There is tremendous interest in the development of pharmacological agents which could antagonize the receptor-mediated actions of VEGFs (Martiny-Baron and Marme, *Curr. Opin. Biotechnol.* 6: 675-680, 1995). Monoclonal antibodies to VEGF have been shown to suppress tumor growth in vivo by inhibiting tumor-associated angiogenesis (Kim et al., *Nature* 362: 841-844, 1993). Similar inhibitory effects on tumor growth have been observed in model systems resulting from expression of either antisense RNA for VEGF (Saleh et al., *Cancer Res.* 56: 393-401, 1996) or a dominant-negative VEGFR-2 mutant (Millauer et al., *Nature* 367: 576-579, 1994).

However, tumor inhibition studies with neutralizing antibodies suggested that other angiogenic factors besides VEGF may be involved (Kim, K. et al., *Nature* 362: 841-844, 1993). Furthermore, the activity of angiogenic factors other than VEGF in malignant melanoma is suggested by the finding that not all melanomas express VEGF (Issa, R. et al., *Lab Invest* 79: 417-425, 1999).

The biological functions of the different members of the VEGF family are currently being elucidated. Of particular interest are the properties of VEGF-D and VEGF-C. These proteins bind to both VEGFR-2 and VEGFR-3—localized on vascular and lymphatic endothelial cells respectively—and are closely related in primary structure (48% amino acid identity). Both factors are mitogenic for endothelial cells in vitro. VEGF-C has been shown to be angiogenic in the mouse cornea model and in the avian chorioallantoic membrane (Cao et al., *Proc. Natl. Acad. Sci. USA* 95: 14389-14394, 1998) and was able to induce angiogenesis in the setting of tissue ischemia (Witzenbichler et al., *Am. J. Pathol.* 153: 381-394, 1998). Furthermore, VEGF-C stimulated lymphangiogenesis in the avian chorioallantoic membrane (Oh et al., *Dev. Biol.* 188: 96-109, 1997) and in a transgenic mouse model (Jeltsch et al., *Science* 276: 1423-1425, 1997). VEGF-D was shown to be angiogenic in the rabbit cornea (Marconcini et al., *Proc. Natl. Acad. Sci. USA* 96: 9671-9676, 1999). The lymphangiogenic capacity of VEGF-D has been reported (Veikkola et al., *EMBO J*, 20:1223-1231, 2001), confirming assumptions that VEGF-D, like VEGF-C, binds and activates VEGFR-3, a receptor thought to signal for lymphangiogenesis (Taipale et al., *Cur. Topics Micro. Immunol.* 237: 85-96, 1999). VEGF-D tumor lymphangiogenesis has also been reported (Stacker, et al., *Nature Med*, 7:186-191, 2001). VEGF-D and VEGF-C may be of particular importance for the malignancy of tumors, as metastases can spread via either blood vessels or lymphatic vessels; therefore molecules which stimulate angiogenesis or lymphangiogenesis could contribute toward malignancy. This has already been shown to be the case for VEGF. It is noteworthy that VEGF-D gene expression is induced by c-fos, a transcription factor known to be important for malignancy (Orlandini et al., *Proc. Natl. Acad. Sci. USA* 93: 11675-11680, 1996). It is speculated that the mechanism by which c-Fos contributes to malignancy is the upregulation of genes encoding angiogenic factors. Tumor cells deficient in c-fos fail to undergo malignant progression, possibly due to an inability to induce angiogenesis (Saez, E. et al., *Cell* 82: 721-732, 1995). This indicates the existence of an angiogenic factor up-regulated by c-fos during tumor progression.

As shown in FIG. 1, the predominant intracellular form of VEGF-D is a homodimeric propeptide that consists of the VEGF Homology Domain (VHD) and the N- and C-terminal propeptides and has the sequence of SEQ ID NO:2. After secretion, this polypeptide is proteolytically cleaved (Stacker, S. A. et al., *J Biol Chem* 274: 32127-32136, 1999). Proteolytic processing (at positions marked by black arrowheads) gives rise to partially processed forms and a fully processed, mature form which consists of dimers of the VHD. The VHD, which has the sequence of SEQ ID NO:3 (i.e. residues 93 to 201 of full length VEGF-D), contains binding sites for both VEGFR-2 and VEGFR-3. The mature form binds both VEGFR-2 and VEGFR-3 with much higher affinity than the unprocessed form (Stacker, S. A. et al., *J Biol Chem* 274: 32127-32136, 1999).

The localization of VEGF-D protein in human cancer has not been studied due to the lack of antibodies specific for the VHD of VEGF-D. Antibodies against the N- or C-terminal propeptides are inappropriate as these regions are cleaved from the bioactive VHD and would localize differently than the VHD (Stacker, S. A. et al., *J Biol Chem* 274: 32127-32136, 1999). Expression data for VEGF-D has been reported in Achen, et al., *J. Pathology*, 193:147-154, 2001.

SUMMARY OF THE INVENTION

The invention generally relates to a method for treating and alleviating melanomas and various cancers, methods for screening for neoplastic diseases, and a method for maintaining vascularization of normal tissue.

According to a first aspect, the present invention provides a method of treating an organism suffering from a neoplastic disease characterized by the expression of VEGF-D by a tumor including, but not limited to, melanomas, breast ductal carcinoma, squamous cell carcinoma, prostate tumors and endometrial cancer. The method comprises screening an organism to determine a presence or an absence of VEGF-D-expressing tumor cells; selecting the organism determined from the screening to have a tumor expressing VEGF-D; and administering an effective amount of a VEGF-D antagonist in the vicinity of said tumor to prevent binding of VEGF-D to its corresponding receptors.

VEGF-D antagonists such as compositions comprising anti-sense nucleic acid or triple-stranded DNA encoding VEGF-D inhibit VEGF-D expression.

Other VEGF-D antagonists that inhibit VEGF-D activity are compounds comprising antibodies and/or competitive or noncompetitive inhibitors of binding of VEGF-D in both dimer formation and receptor binding. These VEGF-D antagonists include a VEGF-D modified polypeptide, as described below, which has the ability to bind to VEGF-D and prevent binding to the VEGF-D receptors or which has the ability to bind the VEGF-D receptors, but which is unable to stimulate endothelial cell proliferation, differentiation, migration or survival. Small molecule inhibitors to VEGF-D, VEGFR-2 or VEGFR-3 and antibodies directed against VEGF-D, VEGFR-2 or VEGFR-3 may also be used.

It is contemplated that some modified VEGF-D polypeptides will have the ability to bind to VEGF-D receptors on cells including, but not limited to, endothelial cells, connective tissue cells, myofibroblasts and/or mesenchymal cells, but will be unable to stimulate cell proliferation, differentiation, migration, motility or survival or to induce vascular proliferation, connective tissue development or wound healing. These modified polypeptides are expected to be able to act as competitive or non-competitive inhibitors of the VEGF-D polypeptides and growth factors of the PDGF/VEGF family, and to be useful in situations where prevention or reduction of the VEGF-D polypeptide or PDGF/VEGF family growth factor action is desirable.

Such receptor-binding but non-mitogenic, non-differentiation inducing, non-migration inducing, non-motility inducing, non-survival promoting, non-connective tissue development promoting, non-wound healing or non-vascular proliferation inducing variants of the VEGF-D polypeptide are also within the scope of the invention, and are referred to herein as "receptor-binding but otherwise inactive variants". Because VEGF-D forms a dimer in order to activate its receptors, it is contemplated that receptor-binding but otherwise inactive variants will include dimers of one monomer which comprises the above-mentioned "receptor-binding but otherwise inactive variants" VEGF-D polypeptide and a second monomer which comprises a wild-type VEGF-D or a wild-type growth factor of the PDGF/VEGF family. These dimers can therefore bind to their corresponding receptors but cannot induce downstream signaling.

It is also contemplated that there are other modified VEGF-D polypeptides that can prevent binding of a wild-type VEGF-D or a wild-type growth factor of the PDGF/VEGF family to its corresponding receptor on cells including, but not limited to, endothelial cells, connective tissue cells (such as fibroblasts), myofibroblasts and/or mesenchymal cells. These dimers will be unable to stimulate endothelial cell proliferation, differentiation, migration, survival, or induce vascular permeability, and/or stimulate proliferation and/or differentiation and/or motility of connective tissue cells, myofibroblasts or mesenchymal cells.

These modified polypeptides are able to act as competitive or non-competitive inhibitors of the VEGF-D growth factor or a growth factor of the PDGF/VEGF family, and are useful in situations where prevention or reduction of the VEGF-D growth factor or PDGF/VEGF family growth factor action is desirable. Such situations include the tissue remodeling that takes place during invasion of tumor cells into a normal cell population by primary or metastatic tumor formation. VEGF-D or PDGF/VEGF family growth factor-binding but non-mitogenic, non-differentiation inducing, non-migration inducing, non-motility inducing, non-survival promoting, non-connective tissue promoting, non-wound healing or non-vascular proliferation inducing variants of the VEGF-D growth factor are therefore within the scope of the invention, and are referred to herein as "the VEGF-D growth factor-dimer forming but otherwise inactive or interfering variants".

Modified forms of the VEGF-D polypeptide can be prepared by targeting essential regions of the VEGF-D polypeptide for modification. These essential regions are expected to fall within the strongly-conserved PDGF/VEGF Homology Domain (VHD). The growth factors of the PDGF/VEGF family, including VEGF, are dimeric, and VEGF, VEGF-B, VEGF-C, VEGF-D, PlGF, PDGF-A and PDGF-B show complete conservation of eight cysteine residues in the VHD (Olofsson et al., Proc. Natl. Acad. Sci. USA, 1996 93 2576-2581; Joukov et al., EMBO J., 1996 15 290-298). These cysteines are thought to be involved in intra- and inter-molecular disulfide bonding.

In addition there are further strongly, but not completely, conserved cysteine residues in the C-terminal domains. Loops 1, 2 and 3 of each VHD subunit, which are formed by intra-molecular disulfide bonding, are involved in binding to the receptors for the PDGF/VEGF family of growth factors (Andersson et al., Growth Factors, 1995 12 159-164). Modified polypeptides can readily be tested for their ability to inhibit the biological activity of VEGF-D by routine activity assay procedures such as the endothelial cell proliferation assay.

VEGF-D antagonists useful in the invention may also include molecules comprising polypeptides corresponding to the VEGF-D binding domains of VEGFR-2 (Flk1) or VEGFR-3 (Flt4). For example, the soluble Ig fusion proteins described in Achen et al., *Proc. Natl. Acad. Sci. USA,* 95: 548-553, 1998, which contain the extracellular domains of human VEGFR-2 and human VEGFR-3 and bind to VEGF-DΔNΔC could suitably be used as VEGF-D antagonists.

The method for treating and alleviating melanomas and various cancers can also occur by targeting a tumor expressing VEGF-D, VEGFR-2 and/or VEGFR-3 for death. This would involve coupling a cytotoxic agent to a polypeptide of the invention, an antibody directed against VEGF-D, VEGFR-2 or VEGFR-3 or a small molecule directed against VEGF-D, VEGFR-2 or VEGFR-3 in order to kill a tumor expressing VEGF-D, VEGFR-2 and/or VEGFR-3. Such cytotoxic agents include, but are not limited to, plant toxins (e.g. ricin A chain, saporin), bacterial or fungal toxins (e.g. diphtheria toxin) or radionucleotides (e.g. 211-Astatine, 212-Bismuth, 90-Yttrium, 131-Iodine, 99-Technitium), alkylating agents (e.g. chlorambucil), anti-mitotic agents (e.g. vinca alkaloids), and DNA intercalating agents (e.g. adriamycin).

The polypeptides, VEGF-D antagonists or antibodies which inhibit the biological activity of VEGF-D also may be employed in the form of a pharmaceutically acceptable non-toxic salt thereof, and/or in combination with a pharmaceutically acceptable solid or liquid carrier or adjuvant. A preferred pharmaceutical composition will inhibit or interfere with a biological activity induced by at least VEGF-D.

Examples of such a carrier or adjuvant include, but are not limited to, saline, buffered saline, Ringer's solution, mineral oil, talc, corn starch, gelatin, lactose, sucrose, microcrystalline cellulose, kaolin, mannitol, dicalcium phosphate, sodium chloride, alginic acid, dextrose, water, glycerol, ethanol, thickeners, stabilizers, suspending agents and combinations thereof. Such compositions may be in the form of solutions, suspensions, tablets, capsules, creams, salves, elixirs, syrups, wafers, ointments or other conventional forms. The formulation can, of course, be adjusted in accordance with known principles to suit the mode of administration. Compositions comprising a peptide of the invention will contain from about 0.1% to 90% by weight of the active compound(s), and most generally from about 10% to 30%.

The dose(s) and route of administration will depend upon the nature of the patient and condition to be treated, and will be at the discretion of the attending physician or veterinarian. Suitable routes include oral, subcutaneous, intramuscular, intraperitoneal or intravenous injection, parenteral, topical application, implants etc. For example, an effective amount of a peptide of the invention or antibody is administered to an organism in need thereof in a dose between about 0.1 and 100 mg/kg body weight, and more preferably 1 to 10 mg/kg body weight.

For humanized antibodies, which typically exhibit a long circulating half-life, dosing at intervals ranging from daily to every month, and more preferably every week, or every other week, or every third week, are specifically contemplated. Monitoring the progression of the therapy, patient side effects, and circulating antibody levels will provide additional guidance for an optimal dosing regimen. Data from published and ongoing clinical trials for other antibody-based cancer therapeutics (e.g. anti-HER2, anti-EGF receptor) also provide useful dosage regimen guidance. Topical application of VEGF-D may be used in a manner analogous to VEGF.

According to a second aspect, the invention provides a method for screening for and/or diagnosing a neoplastic disease characterized by an increase in blood vessel vascular endothelial cells in or around a neoplastic growth. The method comprises obtaining a sample from an organism suspected of being in a neoplastic disease state characterized by an increase in blood vessel vascular endothelial cells in or around a neoplastic growth; exposing said sample to a composition comprising a compound that specifically binds VEGF-D; washing said sample; and screening for said disease by detecting the presence, quantity or distribution of said compound in said sample, where detection of VEGF-D in or on vascular blood vessel endothelial cells in and around a potential neoplastic growth is indicative of a neoplastic disease.

This method can further comprise exposing the sample to a second compound that specifically binds to VEGFR-2 and/or VEGFR-3, and wherein the screening step comprises detection of the compound that binds VEGF-D and the second compound bound to blood vessel vascular endothelial cells, to determine the presence, quantity or distribution of blood vessel vascular endothelial cells having both VEGF-D and VEGFR-2 and/or VEGFR-3 in and around a potential neoplastic growth.

It will be clearly understood that for the purposes of this specification the term "sample" includes, but is not limited to, obtaining a sample of tissue, blood, serum, plasma, urine, ascities fluid or pleural effusion. Preferably the tissue is human tissue. The compound is preferably a monoclonal antibody. It will be appreciated that use of the second compound helps the practitioner to confirm that the VEGF-D found on the vessels in or near the tumor arises due to receptor-mediated uptake, which supports the hypothesis that VEGF-D, secreted by tumor cells, binds and accumulates in target endothelial cells thereby establishing a paracrine mechanism regulating tumor angiogenesis.

According to a third aspect, the invention provides a method for screening for and/or diagnosing a neoplastic disease characterized by an increase in expression of VEGF-D. The method comprises obtaining a sample from an organism suspected of being in a disease state characterized by an increase in expression of VEGF-D; exposing said sample to a composition comprising a compound that specifically binds VEGF-D; washing said sample; and screening for said disease by detecting the presence, quantity or distribution of said compound in said sample, where detection of VEGF-D in cells in and around a potential neoplastic growth is indicative of a neoplastic disease or VEGF-D in or on blood vessel endothelial cells in and around a potential neoplastic growth is indicative of a neoplastic disease.

According to a fourth aspect, the invention provides a method for screening for and/or diagnosing a neoplastic disease characterized by a change in lymph vessel endothelial cells. The method comprises obtaining a sample from an organism suspected of being in a disease state characterized by an increase in lymph vessel endothelial cells; exposing said sample to a composition comprising a compound that specifically binds VEGF-D; washing said sample; and screening for said disease by detecting the presence, quantity or distribution of said compound in said tissue sample, where detection of VEGF-D on or in lymphatic endothelial cells in and around a potential neoplastic growth is indicative of a neoplastic disease.

This method can further comprise exposing the tissue sample to a second compound that specifically binds to VEGFR-3, and wherein the screening step comprises detection of the compound that binds VEGF-D and the second compound bound to lymph vessel endothelial cells, to determine the presence, quantity or distribution of lymph vessel endothelial cells having both VEGF-D and VEGFR-3 in and around a potential neoplastic growth.

It will be appreciated that use of the second compound helps the practitioner to confirm that the VEGF-D found on the lymphatic vessels in or near the tumor arises due to receptor- mediated uptake, which supports the hypothesis that VEGF-D, secreted by tumor cells, binds and accumulates in target lymphatic endothelial cells thereby establishing a paracrine mechanism regulating tumor lymphangiogenesis.

According to a fifth aspect, the invention provides a method for maintaining the vascularization of tissue in an organism, comprising administering to said organism in need of such treatment an effective amount of VEGF-D, or a fragment or analog thereof having the biological activity of VEGF-D.

It is contemplated that the fifth aspect is important where VEGF-D/VEGFs are limiting in the tissues of patients, especially in older patients in whom peripheral vessels may be in a state of atrophy. Treatment with an effective amount of VEGF-D could help maintain the integrity of the vasculature by stimulating endothelial cell proliferation in aging/damaged vessels.

Preferably the VEGF-D is expressed as full length, unprocessed VEGF-D or as the fully processed, mature form of VEGF-D as well as fragments or analogs of both the full length and mature form of VEGF-D which have the biological activity of VEGF-D as herein defined.

It will be clearly understood that for the purposes of this specification the phrase "fully processed VEGF-D" means the mature form of VEGF-D polypeptide, i.e. the VEGF homology domain (VHD), having the sequence of SEQ ID NO:3 which is without the N- and C-terminal propeptides. The phrase "proteolytically processed form of VEGF-D" means a VEGF-D polypeptide without the N- and/or C-terminal propeptide, and the phrase "unprocessed VEGF-D" means a full-length VEGF-D polypeptide having the sequence of SEQ ID NO:2 with both the N- and C-terminal propeptides.

The full length VEGF-D polypeptide having the sequence of SEQ ID NO:2 may be optionally linked to the FLAG® peptide. Where the full length VEGF-D polypeptide is linked to FLAG®, the fragment is referred to herein as VEGF-D-FULL-N-FLAG. A preferred fragment of VEGF-D is the portion of VEGF-D from amino acid residue 93 to amino acid residue 201 (i.e. the VHD (SEQ ID NO:3)), optionally linked to the FLAG® peptide. Where the fragment is linked to FLAG®, the fragment is referred to herein as VEGF-DΔ-NΔC.

The expression "biological activity of VEGF-D" is to be understood to mean the ability to stimulate one or more of endothelial cell proliferation, differentiation, migration, survival or vascular permeability. Reports suggest, however, that VEGF-D may not have vascular permeability activity (Stacker, et al., *JBC*, 274:34884-34892, 1999).

Polypeptides comprising conservative substitutions, insertions, or deletions, but which still retain the biological activity of VEGF-D are clearly to be understood to be within the scope of the invention. Persons skilled in the art will be well aware of methods which can readily be used to generate such polypeptides, for example the use of site-directed mutagenesis, or specific enzymatic cleavage and ligation. The skilled person will also be aware that peptidomimetic compounds or compounds in which one or more amino acid residues are replaced by a non-naturally occurring amino acid or an amino acid analog may retain the required aspects of the biological activity of VEGF-D. Such compounds can readily be made and tested by methods known in the art, and are also within the scope of the invention.

Preferably where amino acid substitution is used, the substitution is conservative, i.e. an amino acid is replaced by one of similar size and with similar charge properties.

As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid.

As such, it should be understood that in the context of the present invention, a conservative substitution is recognized in the art as a substitution of one amino acid for another amino acid that has similar properties. Exemplary conservative substitutions are set out in the following Table A from WO 97/09433.

TABLE A

| Conservative Substitutions I | |
|---|---|
| SIDE CHAIN CHARACTERISTIC | AMINO ACID |
| Aliphatic | |
| Non-polar | G A P |
|  | I L V |
| Polar - uncharged | C S T M |
|  | N Q |
| Polar - charged | D E |
|  | K R |
| Aromatic | H F W Y |
| Other | N Q D E |

Alternatively, conservative amino acids can be grouped as described in Lehninger, [Biochemistry, Second Edition; Worth Publishers, Inc. NY:NY (1975), pp. 71-77] as set out in the following Table B.

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Exemplary conservative substitutions are set out in the following Table C.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

Possible variant forms of the VEGF-D polypeptide which may result from alternative splicing, as are known to occur with VEGF and VEGF-B, and naturally-occurring allelic variants of the nucleic acid sequence encoding VEGF-D are encompassed within the scope of the invention. Allelic variants are well known in the art, and represent alternative forms of a nucleic acid sequence which comprise substitution, deletion or addition of one or more nucleotides, but which do not result in any substantial functional alteration of the encoded polypeptide.

Such variant functional forms of VEGF-D can be prepared by targeting non-essential regions of the VEGF-D polypeptide for modification. These non-essential regions are expected to fall outside the strongly-conserved regions. In particular, the growth factors of the PDGF/VEGF family, including VEGF, are dimeric, and VEGF, VEGF-B, VEGF-C, VEGF-D, PlGF, PDGF-A and PDGF-B show complete conservation of eight cysteine residues in the N-terminal domains, i.e. the PDGF/VEGF-like domains (Olofsson et al., Proc. Natl. Acad. Sci. USA, 1996 93 2576-2581; Joukov et al., EMBO J., 1996 15 290-298). These cysteines are thought to be involved in intra- and inter-molecular disulfide bonding.

In addition there are further strongly, but not completely, conserved cysteine residues in the C-terminal domains. Loops 1, 2 and 3 of each VHD subunit, which are formed by intra-molecular disulfide bonding, are involved in binding to the receptors for the PDGF/VEGF family of growth factors (Andersson et al., Growth Factors, 1995 12 159-164).

Persons skilled in the art thus are well aware that these cysteine residues should be preserved in any proposed functional variant form, and that the active sites present in loops 1, 2 and 3 also should be preserved. However, other regions of the molecule can be expected to be of lesser importance for biological function, and therefore offer suitable targets for modification. Modified polypeptides can readily be tested for their ability to show the biological activity of VEGF-D by routine activity assay procedures such as the endothelial cell proliferation assay.

It has been shown that a strong signal for VEGF-D is present in a subset of hematopoetic cells. These cells flood into the peripheral regions of some tumors in a type of inflammatory response. Thus, inhibition of this process would be useful where it is desirable to prevent this inflammatory response. Accordingly, a sixth aspect of the invention provides a method for inhibiting the inflammatory response caused by this subset of hematopoetic cells of these tumors, comprising inhibiting the expression or activity of VEGF-D by this subset of hematopoetic cells. It is contemplated that inhibiting this type of inflammatory response could be used for the treatment of autoimmune diseases, for example, arthritis.

Antibodies according to the invention also may be labeled with a detectable label, and utilized for diagnostic purposes. The antibody may be covalently or non-covalently coupled to a suitable supermagnetic, paramagnetic, electron dense, ecogenic or radioactive agent for imaging. For use in diagnostic assays, radioactive or non-radioactive labels may be used. Examples of radioactive labels include a radioactive atom or group, such as $^{125}I$ or $^{32}P$. Examples of non-radioactive labels include enzyme labels, such as horseradish peroxidase, or fluorimetric labels, such as fluorescein-5-isothiocyanate (FITC). Labeling may be direct or indirect, covalent or non-covalent.

In accordance with a further aspect of the invention, the invention relates to a method of treating an organism, e.g. a mammal, suffering from a neoplastic disease characterized by the expression of VEGF-D by a tumor such as malignant melanoma, breast ductal carcinoma, squamous cell carcinoma, prostate cancer or endometrial cancer, comprising administering an effective amount of a VEGF-D antagonist in the vicinity of said tumor to prevent binding of VEGF-D to its corresponding receptor. If desired, a cytotoxic agent may be co-administered with the VEGF-D antagonist. A preferred VEGF-D antagonist is a monoclonal antibody which specifically binds VEGF-D and blocks VEGF-D binding to VEGF Receptor-2 or VEGF Receptor-3, especially an antibody which binds to the VEGF homology domain of VEGF-D.

In yet another aspect, the invention relates to a method of screening a tumor for metastatic risk, comprising exposing a tumor sample to a composition comprising a compound that specifically binds VEGF-D, washing the sample, and screening for metastatic risk by detecting the presence, quantity or distribution of said compound in said sample; the expression of VEGF-D by the tumor being indicative of metastatic risk. A preferred compound for use in this aspect of the invention is a monoclonal antibody which specifically binds VEGF-D, especially an antibody which binds to the VEGF homology domain of VEGF-D and is labelled with a detectable label.

A still further aspect of the invention relates to a method of detecting micro-metastasis of a neoplastic disease state characterized by an increase in expression of VEGF-D, comprising obtaining a tissue sample from a site spaced from a neoplastic growth, such as a lymph node from tissue surrounding said neoplastic growth, in an organism in said neoplastic disease state, exposing the sample to a composition comprising a compound that specifically binds VEGF-D, washing the sample, and screening for said metastasis of said neoplastic disease by detecting the presence, quantity or distribution of said compound in the tissue sample; the detection of VEGF-D in the tissue sample being indicative of metastasis of said neoplastic disease. Again, a preferred compound comprises a monoclonal antibody which specifically binds VEGF-D, especially an antibody which binds to the VEGF homology domain of VEGF-D and which is labelled with a detectable label.

It will be clearly understood that for the purposes of this specification the word "comprising" means "including but not limited to". The corresponding meaning applies to the word "comprises".

BRIEF DESCRIPTION OF THE DRAWINGS

FIG. 3 shows autoradiographs taken after two days of exposure to mouse 15.5 days post-coital tissue sections hybridized with VEGF-D antisense and sense RNAs;

DETAILED DESCRIPTION OF PREFERRED EMBODIMENTS

EXAMPLE 1

Figure 1:
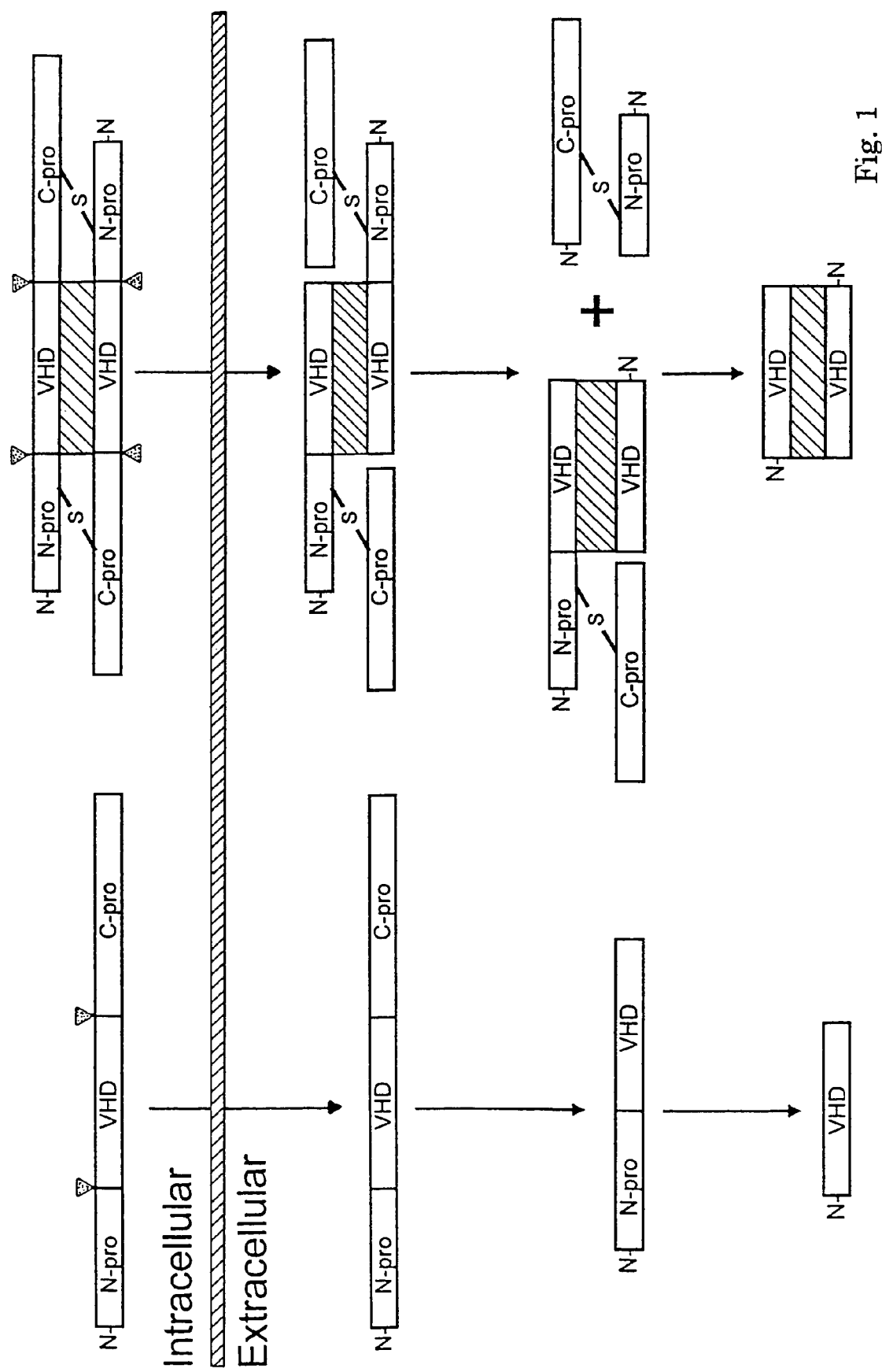
FIG. 1 is a schematic representation of VEGF-D processing.

Production of Monoclonal Antibodies that Bind to Human VEGF-D

In order to detect the VEGF Homology Domain (VHD) rather than the N- and C-terminal propeptides, monoclonal antibodies to the mature form of human VEGF-D (residues 93 to 201 of full-length VEGF-D (SEQ ID NO:2), i.e. with the N- and C-terminal regions removed) were raised in mice. A DNA fragment encoding residues 93 to 201 was amplified by polymerase chain reaction (PCR) with Pfu DNA polymerase, using as template a plasmid comprising full-length human VEGF-D cDNA (SEQ ID NO:1).

The amplified DNA fragment, the correctness of which was confirmed by nucleotide sequencing, was then inserted into the expression vector pEFBOSSFLAG (a gift from Dr. Clare McFarlane at the Walter and Eliza Hall Institute for Medical Research (WEHI), Melbourne, Australia) to give rise to a plasmid designated pEFBOSVEGF-DΔNΔC. The pEF-BOSSFLAG vector contains DNA encoding the signal sequence for protein secretion from the interleukin-3 (IL-3) gene and the FLAG® octapeptide (Sigma-Aldrich). The FLAG® octapeptide can be recognized by commercially available antibodies such as the M2 monoclonal antibody (Sigma-Aldrich). The VEGF-D PCR fragment was inserted into the vector such that the IL-3 signal sequence was immediately upstream from the FLAG® octapeptide, which was in turn immediately upstream from the truncated VEGF-D sequence. All three sequences were in the same reading frame, so that translation of mRNA resulting from transfection of pEFBOSVEGF-DΔNΔC into mammalian cells would give rise to a protein which would have the IL-3 signal sequence at its N-terminus, followed by the FLAG® octapeptide and the truncated VEGF-D sequence.

Cleavage of the signal sequence and subsequent secretion of the protein from the cell give rise to a VEGF-D polypeptide which is tagged with the FLAG® octapeptide adjacent to the N-terminus. VEGF-DΔNΔC was purified by anti-FLAG® affinity chromatography from the medium of COS cells which had been transiently transfected with the plasmid pEF-BOSVEGF-DΔNΔC. (see Example 9 in International Patent Application No. PCT/US97/14696).

Purified VEGF-DΔNΔC was used to immunize female Balb/C mice on day 85 (intraperitoneal), 71 (intraperitoneal) and 4 (intravenous) prior to the harvesting of the spleen cells from the immunized mice and subsequent fusion of these spleen cells to mouse myeloma P3X63Ag8.653 (NS-1) cells. For the first two immunizations, approximately 10 μg of VEGF-DΔNΔC in a 1:1 mixture of PBS and TiterMax adjuvant (#R-1 Research adjuvant; CytRx Corp., Norcross, Ga.) were injected, whereas for the third immunization 35 μg of VEGF-DΔNΔC in PBS was used.

Monoclonal antibodies to VEGF-DΔNΔC were selected by screening the hybridomas on purified VEGF-DΔNΔC using an enzyme immunoassay. Briefly, 96-well microtiter plates were coated with VEGF-DΔNΔC, and hybridoma supernatants were added and incubated for 2 hours at 4° C., followed by six washes in PBS with 0.02% Tween 20. Incubation with a horse radish peroxidase conjugated anti-mouse Ig (Bio-Rad, Hercules, Calif.) followed for 1 hour at 4° C. After washing, the assay was developed with an 2,2'-azino-di-(3-ethylbenz-thiazoline sulfonic acid) (ABTS) substrate system (Zymed, San Francisco, Calif.), and the assay was quantified by reading absorbance at 405 nm in a multiwell plate reader (Flow Laboratories MCC/340, McLean, Va.).

Six antibodies were selected for further analysis and were subcloned twice by limiting dilution. These antibodies were designated 2F8, 3C10, 4A5, 4E10, 4H4 and 5F12. The isotypes of the antibodies were determined using an Isostrip™ isotyping kit (Boehringer Mannheim, Indianapolis, Ind.). Antibodies 2F8, 4A5, 4E10 and 5F12 were of the $IgG_1$ class whereas 4H4 and 3C10 were of the IgM class. All six antibodies contained the kappa light chain.

Hybridoma cell lines were grown in DMEM containing 5% v/v IgG-depleted serum (Gibco BRL, Gaithersburg, Md.), 5 mM L-glutamine, 50 μg/ml gentamicin and 10 μg/ml recombinant IL-6. Antibodies 2F8, 4A5, 4E10 and 5F12 were purified by affinity chromatography using protein G-Sepharose according to the technique of Darby et al., *J. Immunol. Methods* 159: 125-129, 1993, and the yield assessed by measuring absorption at 280 nm.

EXAMPLE 2

Specificity of MAb 4A5

The specificity of MAb 4A5 (renamed VD1) for the VHD of human VEGF-D was assessed by Western blot analysis. Derivatives of VEGF-D used were VEGF-DΔNΔC, consisting of amino acid residues 93 to 201 of human VEGF-D tagged at the N-terminus with the FLAG® octapeptide (Example 1), VEGF-D-FULL-N-FLAG, consisting of full-length VEGF-D tagged at the N-terminus with FLAG® (Stacker, S. A. et al., *J Biol Chem* 274: 32127-32136, 1999), and VEGF-D-CPRO, consisting of the C-terminal propeptide, from amino acid residues 206 to 354, which was also tagged with FLAG® at the N-terminus.

These proteins were expressed in 293-EBNA-1 cells, purified by affinity chromatography with M2 (anti-FLAG®) MAb (IBI/Kodak, New Haven, Conn.) using the procedure set forth in Achen, M. et al., *Proc Natl Acad Sci USA* 95: 548-553, 1998. Fifty nanograms of purified VEGF-D-FULL-N-FLAG (FN), VEGF-DΔNΔC (ΔΔ), and VEGF-D-CPRO (CP) were analyzed by SDS-PAGE (reducing) and by Western blot using the VD1 MAb and a biotinylated M2 MAb as control (the antibody used for blotting is indicated at the bottom of the panel of FIG. 2). SDS-PAGE and Western blot analyses were carried out as described in Stacker, S. A. et al., *J Biol Chem* 274: 32127-32136, 1999.

Figure 2:
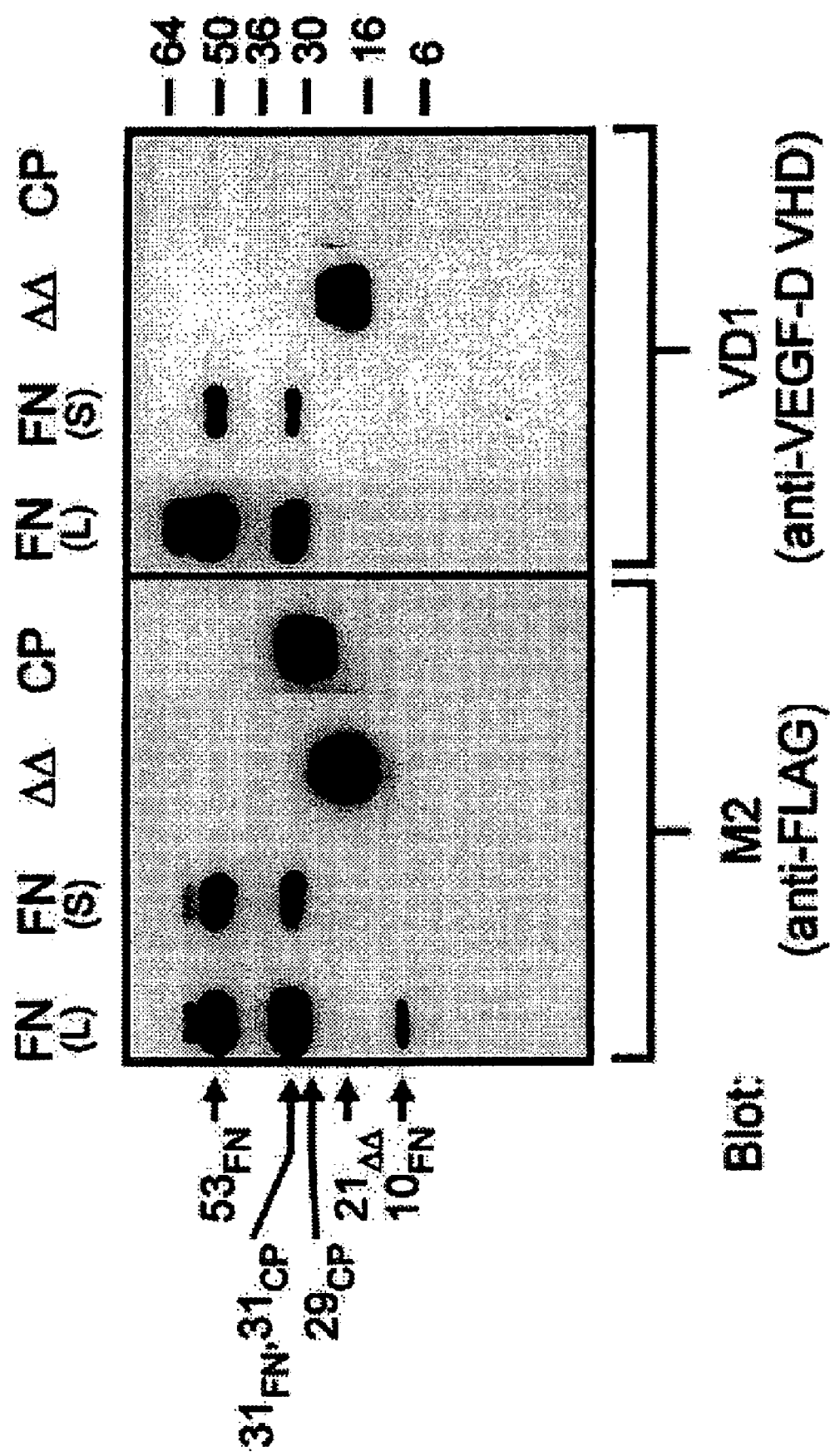
FIG. 2 shows the specificity of MAb 4A5 for the VEGF/PDGF Homology Domain (VHD) of human VEGF-D as assessed by Western blot analysis.

As shown in FIG. 2, the predominant species in the sample of VEGF-D-FULL-N-FLAG consist of unprocessed VEGF-D (Mr ~53 K), partially processed VEGF-D containing both the N-terminal propeptide and the VHD (~31 K), and the N-terminal propeptide (~10 K) (Stacker, S. A. et al., *J Biol Chem* 274: 32127-32136, 1999), all of which are detected with the M2 MAb as they are tagged with the FLAG® octapeptide (arrows to the left, numbers represent Mr in K and subscripts indicate the sample in which the band is detected).

Likewise, VEGF-DΔNΔC (~21 K) and VEGF-D-CPRO (two bands of ~31 and ~29 K which arise due to differential glycosylation) are detected with M2 (arrows to the left) as these polypeptides are also tagged with FLAG®. VD1 detects unprocessed VEGF-D, partially processed VEGF-D and VEGF-DΔNΔC, but not the N-terminal propeptide (~10 K) in the VEGF-D-FULL-N-FLAG preparation, nor the C-terminal propeptide in the VEGF-D-CPRO sample (~31 and ~29 K). Results with VEGF-D-FULL-N-FLAG were analyzed with long (L) and short (S) exposures. The positions of molecular weight markers are shown to the right in FIG. 2.

Thus MAb VD1 binds unprocessed VEGF-D, partially processed forms containing the VHD and fully processed VEGF-D, but not the N- or C-terminal propeptides. Furthermore, MAb VD1 was able to immunoprecipitate native human VEGF-DΔNΔC, but not the VHD of human VEGF-C (VEGF-CΔNΔC) (Joukov, V. et al., *EMBO J*, 16: 3898-3911, 1997) in an enzyme immunoassay indicating that VD1 is specific for VEGF-D.

EXAMPLE 3

In Situ Hybridization Studies of VEGF-D Gene Expression in Mouse Embryos

The pattern of VEGF-D gene expression was studied by in situ hybridization using a radiolabeled antisense RNA probe corresponding to nucleotides 1 to 340 of the mouse VEGF-D1 cDNA (SEQ ID NO:4). The antisense RNA was synthesized by in vitro transcription with T3 RNA polymerase and [$^{35}$S] UTPαs. Mouse VEGF-D is fully described in International Patent application PCT/US97/14696 (WO 98/07832). This antisense RNA probe was hybridized to paraffin-embedded tissue sections of mouse embryos at post-coital day 15.5. The labeled sections were subjected to autoradiography for 2 days.

The resulting autoradiographs for sections hybridized to the antisense RNA and to complementary sense RNA (as negative control) are shown in FIG. 3. In FIG. 3, "L" denotes lung and "Sk" denotes skin, and the two tissue sections shown are serial sections. Strong signals for VEGF-D mRNA were detected in the developing lung and associated with the skin. No signals were detected using the control sense RNA.

Figure 4:
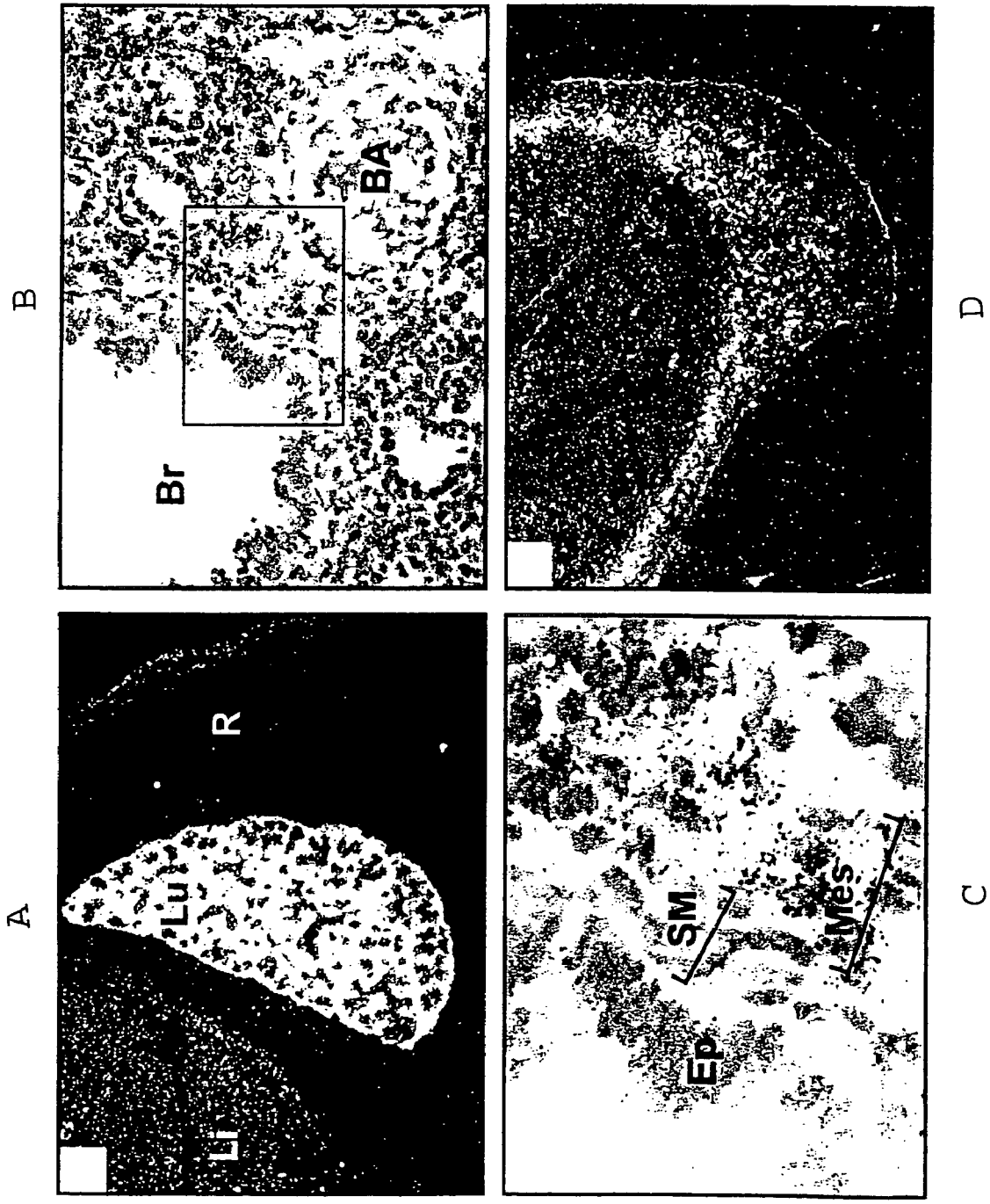
FIGS. 4A-4D show the results of analysis of the distribution of VEGF-D mRNA in the post-coital day 15.5 mouse embryo by in situ hybridization.

In FIGS. 4A-4D, sagittal tissue sections were hybridized with the VEGF-D antisense RNA probe and subsequently incubated with photographic emulsion, developed and stained. The magnification for FIGS. 4A and 4D is ×40, for FIG. 4B, it is ×200 and for FIG. 4C, it is ×500.

In FIG. 4A, the dark field micrograph shows a strong signal for VEGF-D mRNA in lung (Lu). Liver (Li) and ribs (R) are also shown. FIG. 4B shows a higher magnification of the lung. This light field micrograph shows a bronchus (Br) and a bronchial artery (BA). The black outline of a rectangle denotes the region of the section shown in FIG. 4C but at a higher magnification. FIG. 4C shows the epithelial cells of the bronchus (Ep), the developing smooth muscle cells (SM) surrounding the epithelial cell layer and the mesenchymal cells (Mes). The abundance of silver grains associated with mesenchymal cells is apparent.

Thus, microscopic analysis reveals that VEGF-D mRNA is abundant in the mesenchymal cells of the developing lung (FIGS. 4A-4C). In contrast, the epithelial cells of the bronchi and bronchioles are negative, as were the developing smooth muscle cells surrounding the bronchi. The endothelial cells of bronchial arteries are also negative.

In FIG. 4D, a dark field micrograph shows a limb bud. A strong signal was located immediately under the skin in a region of tissue rich in fibroblasts and developing melanocytes.

These results indicate that VEGF-D may attract the growth of blood and lymphatic vessels into the developing lung and into the region immediately underneath the skin. Due to the expression of the VEGF-D gene adjacent to embryonic skin, it is considered that VEGF-D could play a role in inducing the angiogenesis that is associated with malignant melanoma. Malignant melanoma is a very highly vascularized tumor. This suggests that local inhibition of VEGF-D expression, for example using VEGF-D or VEGF receptor-2 or VEGF receptor-3 antibodies, is useful in the treatment of malignant melanoma. Other suitable inhibitors of VEGF-D activity, such as anti-sense nucleic acids or triple-stranded DNA, may also be used.

EXAMPLE 4

Use of Monoclonal Antibodies to Human VEGF-D for Immunohistochemical Analysis of Human Tumors In order to assess the role of VEGF-D in tumor angiogenesis, VEGF-D MAbs, 4A5, 5F12 and 2F8 (renamed VD1, VD2 and VD3, respectively) were used for immunohistochemical analysis of fifteen randomly chosen invasive malignant melanomas. Also used in the analysis were MAbs against human VEGFR-2 (Sigma, St. Louis, Mo.) and polyclonal antibodies against VEGFR-3 (affinity purified anti-human Flt-4 antibodies; R & D Systems, Minneapolis, Minn.). A MAb raised to the receptor for granulocyte colony-stimulating factor, designated LMM774 (Layton et al., *Growth Factors* 14: 117-130, 1997), was used as a negative control. Like the VEGF-D MAbs, LMM774 was of the mouse $IgG_1$ isotype and therefore served as an isotype-matched control antibody.

Five micrometer thick sections from formalin fixed and paraffin embedded tissue of the cutaneous malignant melanomas were used as the test tissue. The sections were dewaxed and rehydrated and then washed with PBS. The primary antibodies were incubated with tissue sections at concentrations of 5-40 g/ml depending on incubation time. Step omission controls, in which primary antibodies were omitted, were carried out in parallel as were adsorption controls in which anti-VEGF-D MAbs were incubated with a 40-fold molar excess of VEGF-DΔNΔC for 1 hour at room temperature prior to incubation with tissue sections.

Isotype-matched controls with the LMM774 antibody were also carried out. Detection of alkaline phosphatase-conjugated secondary antibody was achieved using Fast Red Substrate (Sigma, St. Louis, Mo.). In some cases, tissue sections were bleached of melanin prior to immunohistochemistry by incubation in 0.25% potassium permanganate for 3 hours followed by a six minute incubation in 1% oxalic acid. In these cases, detection of peroxidase-conjugated secondary antibody was with 3,3'-diaminobenzidine (DAB) (Dako Corp., Carpinteria, Calif.).

Positive reactions were seen with all three VEGF-D MAbs with essentially the same staining patterns. VEGF-D immunoreactivity was detected in 13 of the 15 melanomas tested. The melanomas showed patterns of reaction ranging from homogeneous staining throughout the lesion to localization of the reaction at the invasive periphery of the lesion.

FIGS. 5A-5H show the results of immunohistochemical analysis from two tumors exemplifying the different reaction patterns. Antibody detection in FIGS. 5A and 5B was with Fast Red Substrate (red color denotes positive signal), and in FIGS. 5C-5H was with DAB (brown color denotes positive signal). The tissue sections shown in FIGS. 5C-5H were bleached of melanin prior to incubation with antibody. The VEGF-D antibody used in all panels except FIGS. 5E and 5G was VD1 (4A5). Scale bars in FIG. 5A denote 150 μm, in FIGS. 5B-5D 20 μm and in FIGS. 5E-5H 10 μm.

Figure 5:
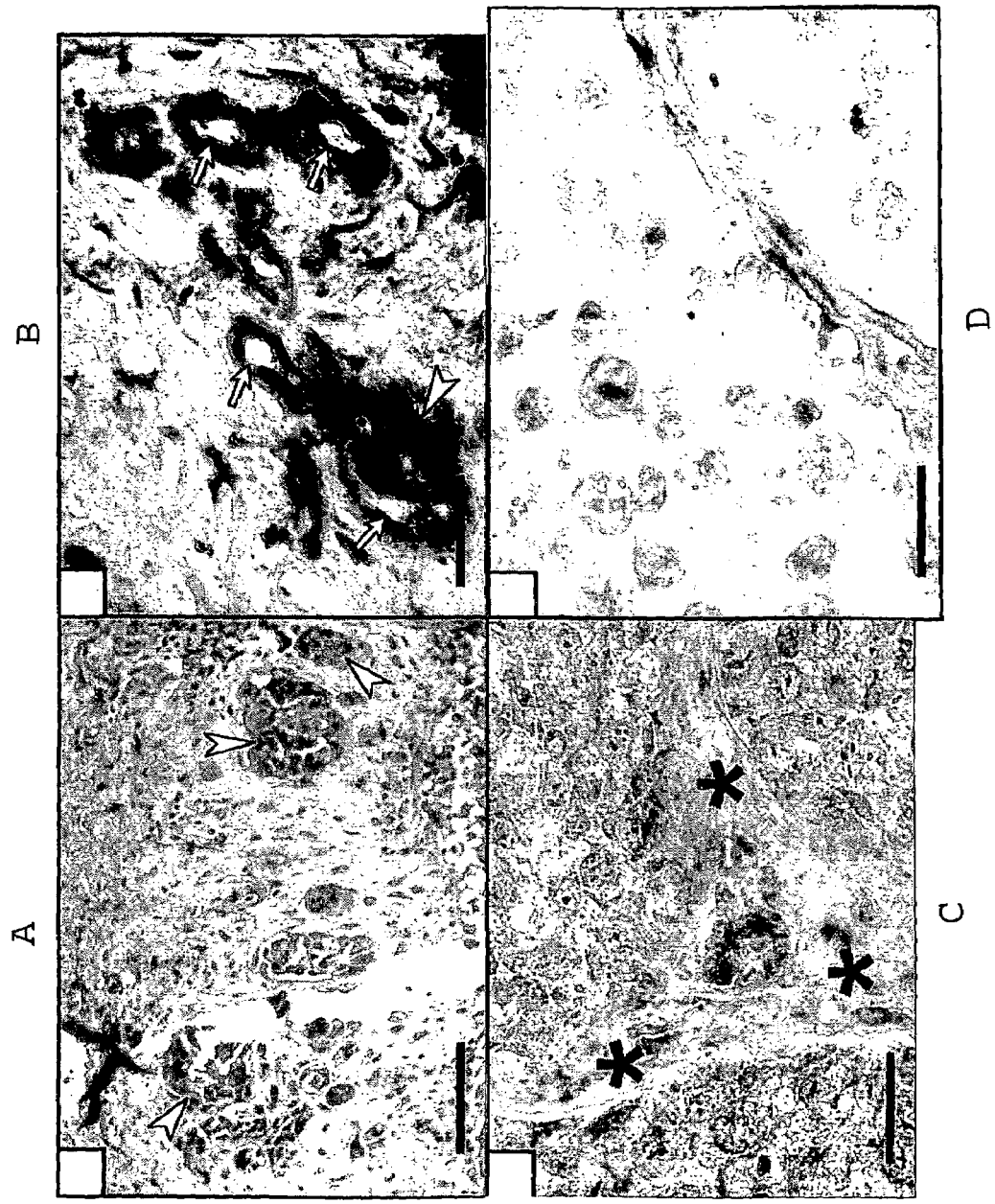
FIGS. 5A-5H show the results of immunohistochemical analysis of two malignant melanomas exemplifying different reaction patterns.
Figure 5:
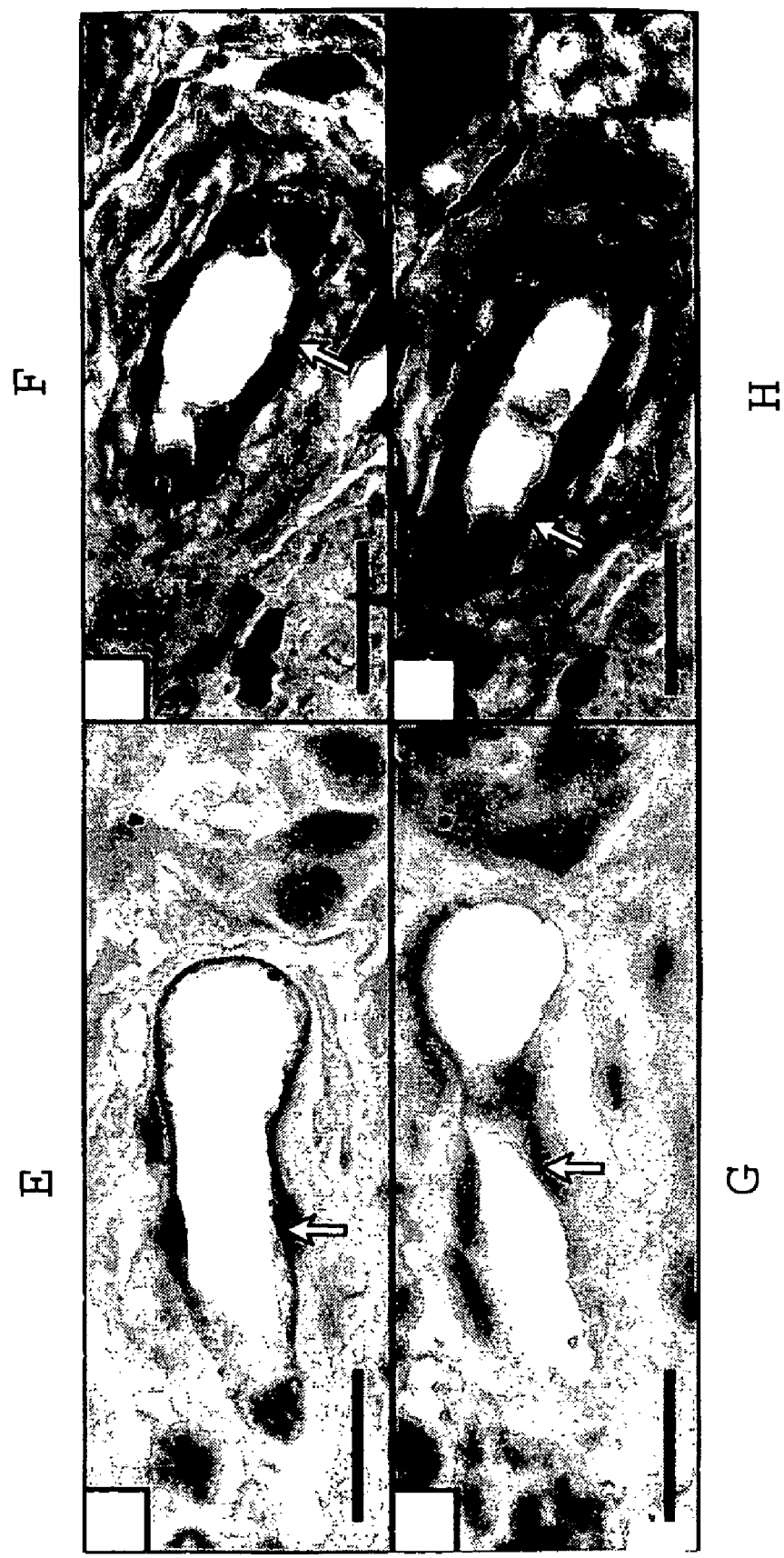

As seen in FIGS. 5A and 5B, heterogeneous staining was apparent through the bulk of the first melanoma. In this tumor, the detected VEGF-D staining is more pronounced in the intradermal nests of tumor cells (white arrowheads) at the periphery of the invasive portions of the main bulk of the tumor, and is less intense or undetectable in the central portion. VEGF-D is also detected in small capillary-sized vessels (white arrows) in the papillary and reticular dermis adjacent to positive reacting tumor cells (FIG. 5B) and in thicker-walled blood vessels of pre-capillary and post-capillary venule size.

As seen in FIG. 5C, in the second melanoma, VEFG-D is more evenly distributed throughout the tumor mass and was detected in vessels in the tumor as well as in tumor cells. Regions of stroma which stained negative are denoted by black asterisks. For both of the above-mentioned tumors, upper dermal capillary vessels and other blood vessels at a distance from the tumor, and in the mid and deep reticular dermis away from the tumor and sweat glands, showed very weak or no vessel wall staining and did not exhibit the granular cytoplasmic endothelial cell staining seen in the small vessels adjacent to the immunoreactive tumor cells. Non-neoplastic junctional melanocytes were also negative indicating that VEGF-D is not expressed by this cell type in adult skin. FIG. 5D, which is a serial section control for the tissue of FIG. 5C, shows that the adsorption control was negative. Step omission and isotype-matched controls were also negative.

Sections of malignant melanoma were analyzed for localization of VEGFR-3, a receptor for VEGF-D which is expressed on the endothelial cells of lymphatic vessels in adult tissues (Lymboussaki, A. et al., *Am. J. Pathol.* 153: 395-403, 1998). As seen in FIG. 5E, VEGFR-3 was detected in the endothelial cells of a thin-walled vessel (white arrow) in the melanoma. The VEGFR-3 positive vessels adjacent to tumor cells were also positive for VEGF-D (FIG. 5F), as assessed by immunohistochemical analysis of serial sections, indicating that the VEGF-D immunoreactivity in these vessels may arise due to receptor-mediated uptake into endothelial cells.

Sections were also analyzed by immunohistochemistry for localization of VEGFR-2. VEGFR-2 is known to be upregulated in the endothelium of blood vessels in tumors (Plate, K. et al., *Cancer Res,* 53: 5822-5827, 1993). As seen in FIG. 5G, VEGFR-2 was detected in the endothelium of blood vessels (white arrow) and in the nearby melanoma. Some of the vessels that were immunopositive for VEGFR-2 were also positive for VEGF-D (white arrow in FIG. 5H) indicating that VEGF-D uptake into tumor vessels could be mediated by this receptor also.

EXAMPLE 5

VEGF-D in Lung Cancer

Neoangiogenesis is thought to be a useful prognostic indicator for non-small cell lung carcinoma (NSCLC) (Fontanini, G. et al., *Clin Cancer Res.* 3: 861-865, 1997). Therefore localization of VEGF-D was analyzed in a case of squamous cell carcinoma of the lung by immunohistochemistry (FIGS. 6A-6F). The immunohistochemistry was conducted as in Example 4, except that antibodies to alpha-smooth muscle actin (DAKO Corp., Carpinteria, Calif.) were also used to immunostain. The anti-VEGF-D MAb used for immunostaining in FIGS. 6A and 6D was VD1 (4A5).

Figure 6:
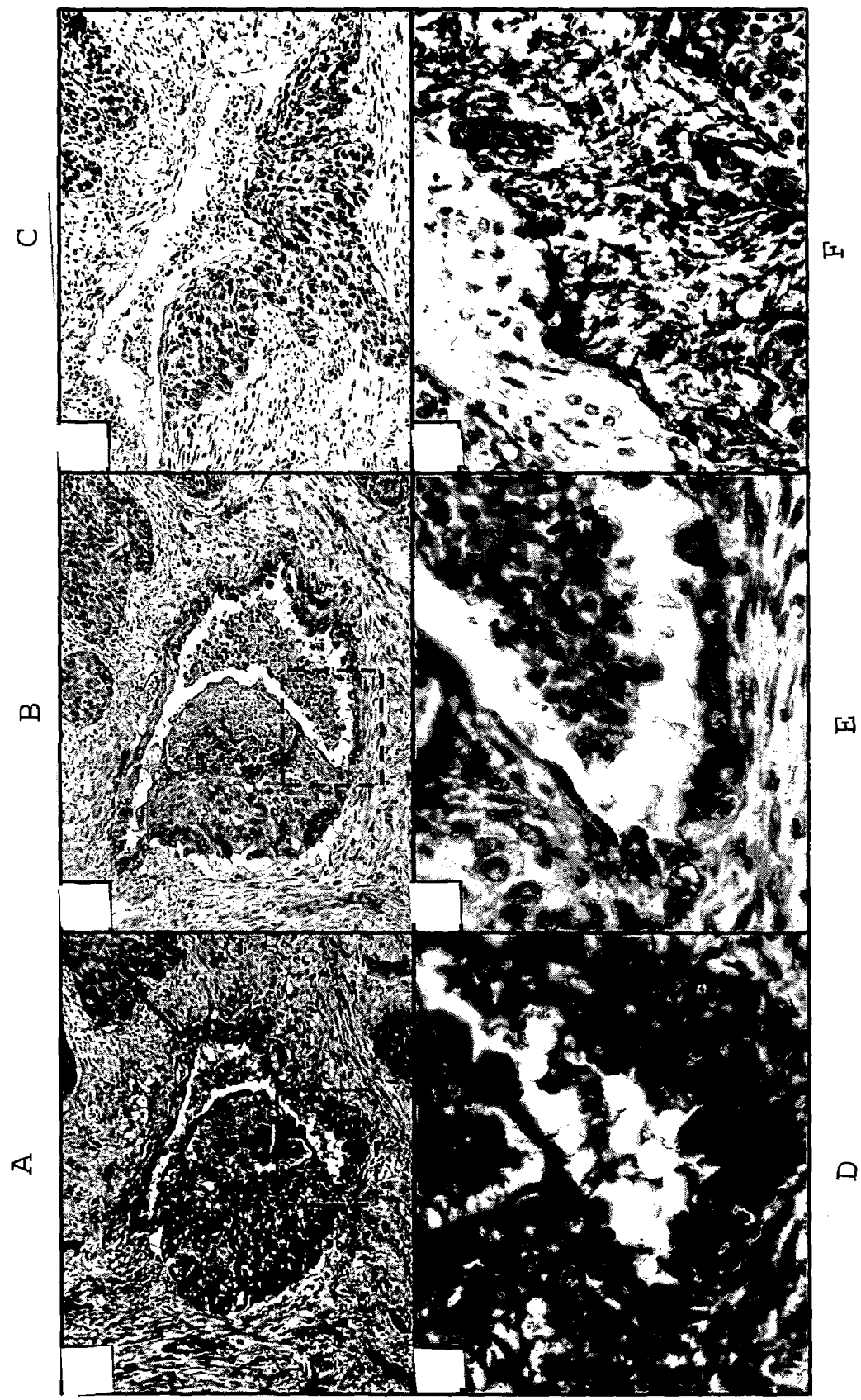
FIGS. 6A-6F show the localization of VEGF-D in squamous cell carcinoma of the lung.

FIG. 6A shows that VEGF-D is detected in tumor cells that form an island at the center of the photomicrograph, in cells lining the adjacent large vessel and in cells within the desmoplastic stroma. The desmoplastic stroma is indicated by a black bracket and the dotted box denotes the region shown in higher power in FIG. 6D. The immunopositive cells in the stroma may be myofibroblasts.

FIG. 6B shows that VEGFR-2 is detected in cells lining the large vessel. However, these vessels were negative for VEGFR-3 in this tumor. The dotted box denotes the region shown in higher power in FIG. 6E. Control staining, of a tissue section from the same case, in which VEGF-D MAb had been preincubated with a 40-fold molar excess of the VHD of human VEGF-D gave no signal (FIG. 6C).

As mentioned above, the immunopositive cells in the desmoplatic stroma may be myofibroblasts. Therefore, the desmoplastic stroma was immunostained using MAbs specific for alpha-smooth muscle actin that detect myofibroblasts. As seen in FIG. 6F, the stroma stained positive, indicating the presence of myofibroblasts. Secretion of an angiogenic factor by stromal components may serve to amplify the angiogenic stimulus generated by the tumor.

EXAMPLE 6

VEGF-D in Breast Cancer

Localization of VEGF-D was also analyzed in breast ductual carcinoma in situ by immunohistochemistry, the results of which are shown in FIGS. 7A-7F. The immunohistochemistry was conducted as in Example 4, except MAbs specific for alpha-smooth muscle actin (DAKO Corp., Carpinteria, Calif.) and the platelet/endothelial adhesion molecule (PE-CAM) (DAKO Corp., Carpinteria, Calif.) were also used to immunostain. The anti-VEGF-D MAb used for immunostaining in FIG. 7A was VD1 (4A5).

Figure 7:
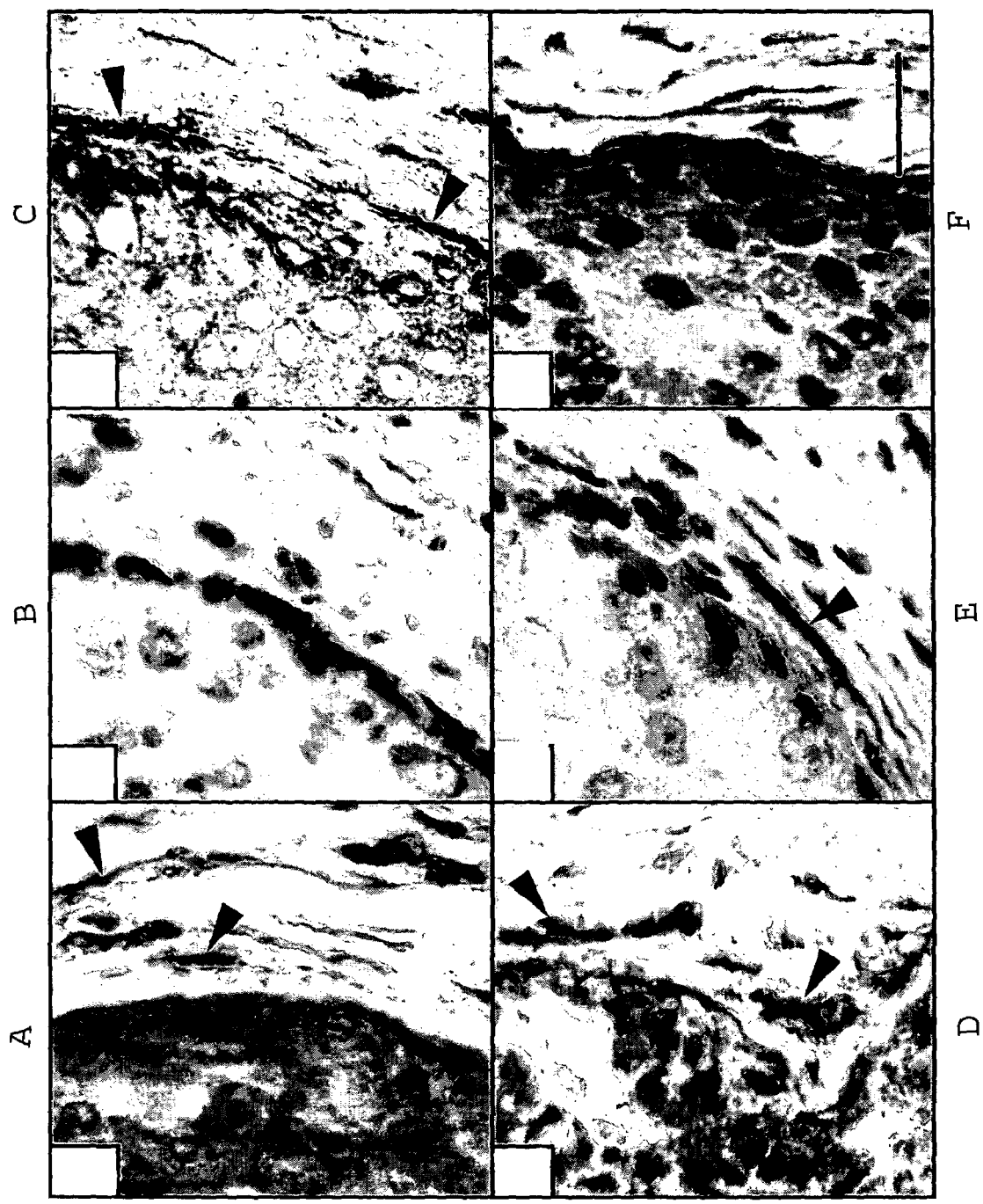
FIGS. 7A-7F show the localization of VEGF-D in breast ductal carcinoma in situ.

As seen in FIG. 7A, VEGF-D was detected in tumor cells in the ducts and in small so-called "necklace" vessels (denoted by black arrowheads) immediately adjacent to the basal lamina of the tumor-filled ducts. The necklace vessels were also positive for VEGFR-2 (FIG. 7C), VEGFR-3 (FIG. 7D) and PECAM (FIG. 7E) as indicated by the black arrowheads. PECAM is a classic marker for endothelium and is also found on platelets and leukocytes. PECAM plays a role in the emigration of leukocytes to inflammatory sites (Muller et al., *J. Exp. Med.* 178: 449-460).

PECAM antibody staining on the "necklace" vessels helps to confirm that these structures are vessels. The edge of the duct is identified by staining for alpha-smooth muscle actin (FIG. 7B) that detects myofibroblasts. Control staining, of a tissue section serial to that shown in FIG. 7A, in which VEGF-D MAb had been preincubated with a 40-fold molar excess of the VHD of human VEGF-D gave no signal (FIG. 7F). These findings indicate that VEGF-D, secreted by the tumor cells, could activate its receptors on vessels in the vicinity and thereby play a role in attracting the growth of the necklace vessels to their positions very close to the ducts. This could be of importance both for solid tumor growth and metastatic spread.

EXAMPLE 7

VEGF-D in Endometrial Cancer

Figure 8:
FIG. 8 shows the localization of VEGF-D in endometrial adenocarcinoma in situ.

VEGF-D was also detected in endometrial adenocarcinoma (FIG. 8). The immunohistochemistry was carried out as in Example 4 using the anti-VEGF-D MAb VD1 (4A5). Moderate staining for VEGF-D was seen in the glandular tumor cells (GL), very strong reactivity was seen in the myofibroblastic cells of the desmoplastic stroma (DM) at the advancing invasive edge of the tumor and strong reactivity in the endothelium and walls of adjacent blood vessels (black arrows) in the myometrium (Myo).

Interestingly, VEGF-D reactivity was particularly strong in the myofibroblasts of the desmoplastic stroma, indicating that the glandular tumor cells can induce VEGF-D expression in these fibroblasts which would amplify the angiogenic potential of the tumor. As expression of VEGF-D in cells of the desmoplastic stroma was also detected in lung carcinoma (FIG. 6A), it may be that a range of tumors can induce VEGF-D in stromal components. This is analogous to the developing lung where the mesenchymal cells, presumably fibroblastic precursors, strongly express the VEGF-D gene. Therefore, signals from both embryonic and tumor tissues can induce expression of VEGF-D in fibroblasts.

EXAMPLE 8

VEGF-D in Non-Tumorigenic Tissue

Tissues with a high cell turn-over and/or metabolic load, such as the colon, require an extensive vascular network. Therefore the human colon was analyzed for localization of VEGF-D by immunohistochemistry, the results of which are shown in FIGS. 9A-9F. The immunohistochemistry was conducted as in Example 4, except that antibodies specific for alpha-smooth muscle actin (DAKO Corp., Carpinteria, Calif.) were also used to immunostain.

For all tissue sections shown, detection was with DAB (brown color denotes positive signal) and for FIGS. 9A, 9B, 9C and 9F, the VEGF-D antibody used was VD1 (4A5). For clarity, counterstaining was omitted in FIGS. 9A, 9B, 9D and 9F. The scale bar in FIG. 9A denotes 120 µm, in FIGS. 9B, 9D and 9F denotes 40 µm and in FIGS. 9C and 9E denotes 6 µm.

Figure 9:
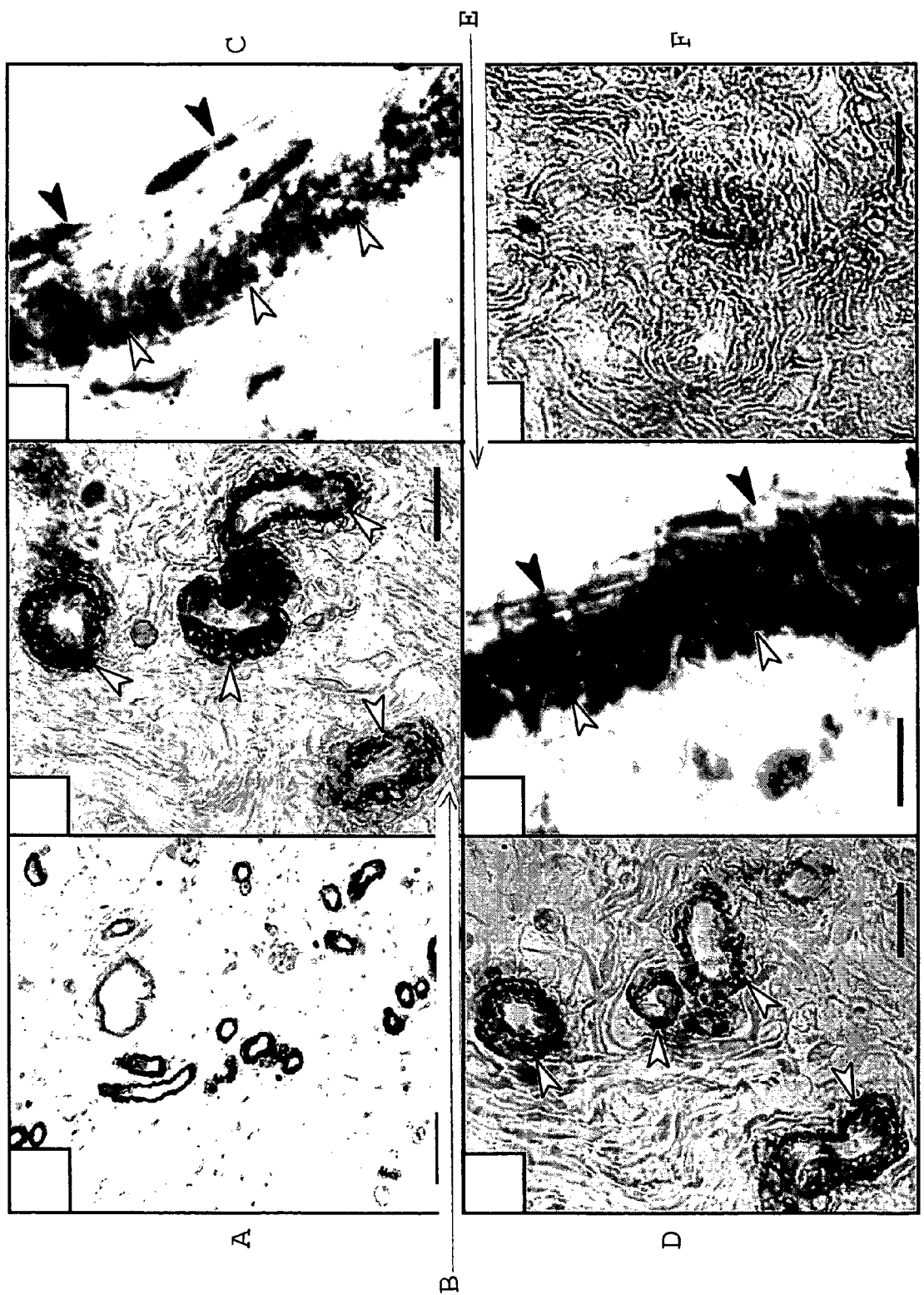
FIGS. 9A-9F show the localization of VEGF-D in normal colon tissue.

VEGF-D was localized in blood vessels of the submucosa (FIG. 9A). Higher power analysis reveals staining of vascular smooth muscle (white arrowheads), but not of the endothelial cells (black arrowheads) in arterioles (FIGS. 9B and 9C). Staining of a serial section to that shown in FIGS. 9A-9C with antibody specific for alpha-smooth muscle actin detects vascular smooth muscle (white arrowheads) but not the endothelium (black arrowheads) (FIGS. 9D and 9E). This staining demonstrates that the VEGF-D reactivity was in vascular smooth muscle cells of arterioles.

Furthermore, these endothelial cells did not exhibit immunoreactivity for either VEGFR-2 or VEGFR-3, indicating that these cells cannot accumulate VEGF-D in a receptor-mediated fashion. Preincubation of the VEGF-D MAb with a 40-fold molar excess of the VHD of human VEGF-D completely blocks the staining of vascular smooth muscle (FIG. 9F).

As the colon is subject to a variety of insults, some of which cause vascular damage, VEGF-D in the submucosa may be produced by vascular smooth muscle cells in preparation for vascular regeneration. Upon activation of the endothelium in response to vascular damage, up-regulation of VEGFR-2 on endothelial cells of these vessels would allow the VEGF-D, produced by the vascular smooth muscle, to induce endothelial cell proliferation and vessel repair. Up-regulation of VEGFR-2 by the endothelium of small arterioles and microvessels in response to arterial damage has been reported previously in the context of ischemic stroke (Issa, R. et al., *Lab Invest* 79: 417-425, 1999).

EXAMPLE 9

Role of VEGF-D in Tumor Development

In order to generate cell lines constitutively over-expressing derivatives of VEGF-D, regions of the human VEGF-D cDNA were inserted into the mammalian expression vector Apex-3 (Evans et al, Mol. Immunol., 1995 32 1183-1195). This vector is maintained episomally when transfected into 293-EBNA human embryonal kidney cells. For expression of mature VEGF-D, the region of pEFBOSVEGF-DΔNΔC containing the sequences encoding the IL-3 signal sequence, the FLAG® octapeptide and the mature VEGF-D were inserted into the XbaI site of Apex-3 (see EXAMPLE 9 in International Patent Application PCT/US97/14696 (WO98/07832)).

The resulting plasmid was designated pVDApexDΔNΔC (Stacker, S. A. et al., *J Biol Chem* 274: 32127-32136, 1999 and see Example 1 in International Patent Application PCT/US98/27373). The entire disclosure of the International Patent Application PCT/US98/27373 is incorporated herein by reference. A similar construct was made for expression of the unprocessed full-length VEGF-D tagged at the N-terminus with Flag®. In this construct, the DNA encoding the VEGF-D signal sequence for protein secretion was deleted and substituted with DNA encoding the IL-3 signal sequence, followed by the FLAG® octapeptide and two amino acids (Thr-Arg) immediately upstream and in the same reading frame as DNA encoding residues 24-354 of VEGF-D. This construct was designated pVDApexFull-N-Flag (Stacker, S. A. et al., *J Biol Chem* 274: 32127-32136, 1999 and see Example 1 in International Patent Application PCT/US98/27373).

These vectors were transfected into cells of the human embryo kidney cell line 293EBNA-1 by the calcium phosphate method or with Fugene® according to the manufacturer's instructions (Roche Molecular Biochemicals, Mannhiem, Germany), and stable transfectants were selected in the presence of 100 µg/ml hygromycin supplemented DMEM. Cell lines expressing high levels of VEGF-D-Full-N-Flag and VEGF-DΔNΔC were subsequently identified by metabolic labeling, immunoprecipitation and Western blot analysis (Stacker, S. A. et al., *J Biol Chem* 274: 32127-32136, 1999 and see Example 1 in International Patent Application PCT/US98/27373).

Six to eight week old SCID mice (ARC, Perth, Australia) were injected subcutaneously in the mammary fat pad with $2 \times 10^7$ of the transfected 293 cells, vector transfected or untransfected parental 293 cells in PBS. Tumors were allowed to grow and were measured with digital calipers over a period of three weeks. Experiments were terminated after three weeks when the first animal reached the maximum size allowed by the Institutional Ethics Committee. The tumor size was calculated as the width×length×0.6×(width×length)/2.

Figure 10:
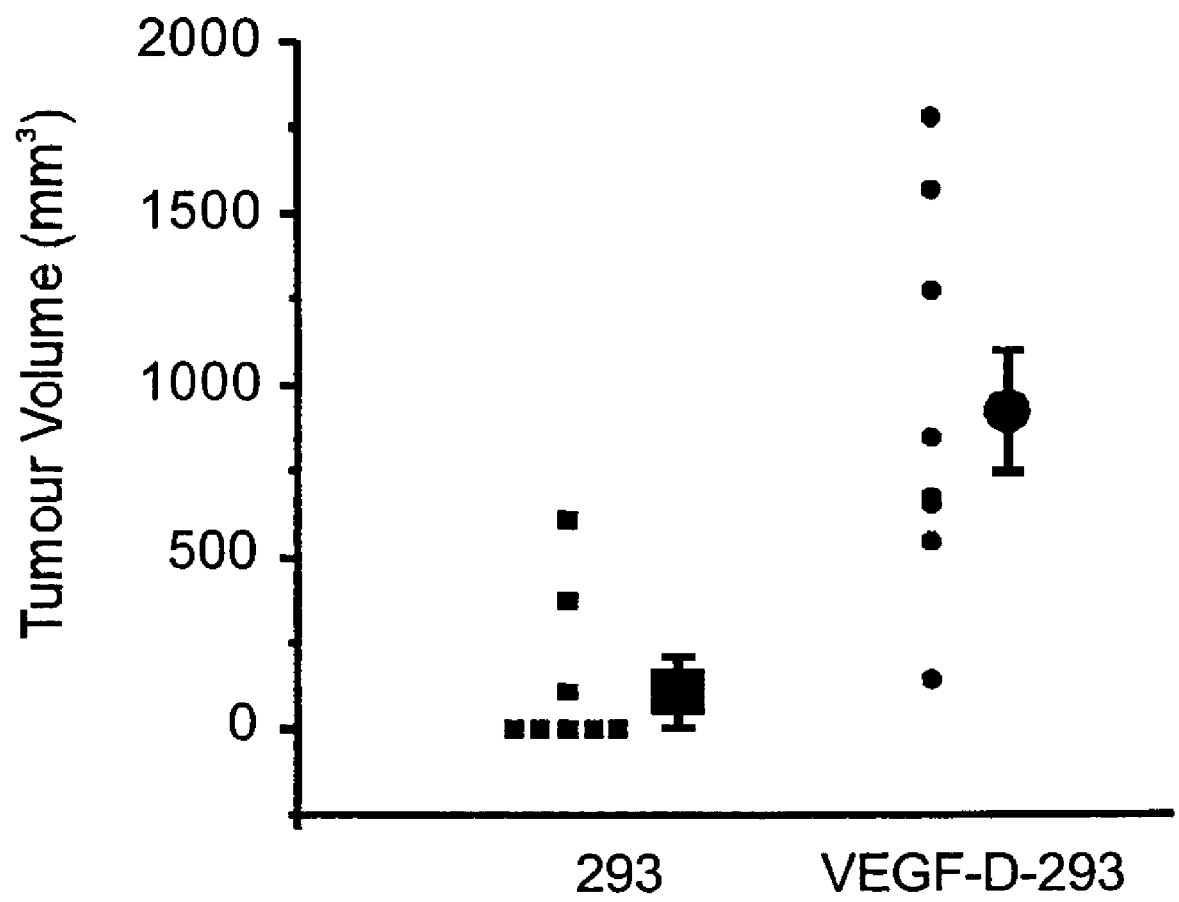
FIG. 10 shows the results of an analysis of tumors in SCID mice resulting from injection of untransfected parental 293 cells (designated "293") and 293 cells transfected with an expression vector encoding VEGF-D-FULL-N-FLAG (designated "VEGF-D-293")

FIG. 10 shows the results of the analysis of tumors in SCID mice resulting from injection of untransfected parental 293 cells (designated "293") or 293 cells transfected with the construct encoding VEGF-D-FULL-N-FLAG (designated "VEGF-D-293"). There is significant difference between the tumors derived from the 293-VEGF-D-FULL-N-FLAG cells and those derived from the untransfected 293 cells. After three weeks the mean tumor size of the 293-VEGF-D-FULL-N-FLAG group was 937±555 mm$^3$ (mean±SD, n=8) compared to 136±230 mm$^3$ for the untransfected 293 cells (n=8). Interestingly, tumors generated from 293 cells transfected with a construct encoding VEGF-DΔNΔC were not significantly different in size, 50±76 mm$^3$ (n=7), to those from the untransfected 293 cells.

In addition, the macroscopic appearance of tumors derived from the untransfected 293 cells was one of a pale white surface, compared to the tumors derived from the 293-VEGF-D-FULL-N-FLAG cells which had a bloody appearance, with the presence of blood vessels apparent throughout the tumor.

Also, sections were analyzed by immunohistochemistry with an anti-PECAM monoclonal antibody (Pharmingen, San Diego, Calif.), a marker of endothelial cells. Sections of tumors generated with 293-VEGF-D-FULL-N-FLAG cells demonstrated a marked increase in PECAM expression compared to the tumors generated with untransfected parental 293 cells. This analysis confirms the much greater abundance of blood vessels in the tumors expressing unprocessed full-length VEGF-D.

This experiment indicates that the unprocessed form of VEGF-D is capable of inducing tumor angiogenesis and the growth of a solid tumor in vivo. Interestingly, the tumors derived from cells expressing the mature, fully processed form of VEGF-D showed no increase in growth compared to the untransfected 293 parental cells. This indicates the importance of the propeptides (N-pro and C-pro) in VEGF-D for the correct localization or function of the VHD of VEGF-D. An explanation for this result is that the propeptides are involved in matrix association and only when VEGF-D is positioned correctly on the extracellular matrix or cell surface heparin sulphate proteoglycans is the growth factor able to induce angiogenesis and/or lymphangiogenesis. An alternative explanation is that the propeptides increase the half-life of the VEGF-D VHD in vivo.

EXAMPLE 10

VEGF-D Induction of Tumor Angiogenesis

To determine whether VEGF-D plays a role in tumor angiogenesis, 293EBNA cell lines expressing VEGF or VEGF-D were generated. 293EBNA cells normally do not express detectable levels of VEGF, VEGF-C, or VEGF-D, the ligands that activate VEGFR-2 and/or VEGFR-3 (Stacker, S. A., et al., *Growth Factors* 17: 1-11 (1999)), see FIG. 11A. 293EBNA cells produce slow growing and poorly vascularized epithelioid-like tumors in immunodeficient mice. Western-blot analysis of conditioned medium from the generated 293EBNA cell lines in vitro showed that the mature forms of the active growth factors were secreted, see FIG. 11B.

Six to twenty-one week old female SCID or SCID/nod mice (Animal Resources Center, Canning Vale, Australia;

Austin Research Institute, Australia; and Walter and Eliza Hall Institute for Medical Research, Australia) were placed in groups of 6 to 10 mice and injected subcutaneously in the mammary fat pad with cell lines expressing VEGF-293, VEGF-D-293, or control 293 cell lines at a concentration of 2.0-2.5×10$^7$ in culture medium. Tumor growth and morphology were analyzed over 35 days. Tumors were measured with digital calipers and tumor volume was calculated by the formula: volume=length×width$^2$×0.52. Three to five weeks after injection with cell lines the mice were euthanized and the tumors were removed for examination. VEGF-D-293 tumors and 293 tumors were excised post mortem on day 25 and weighed.

Figure 11:
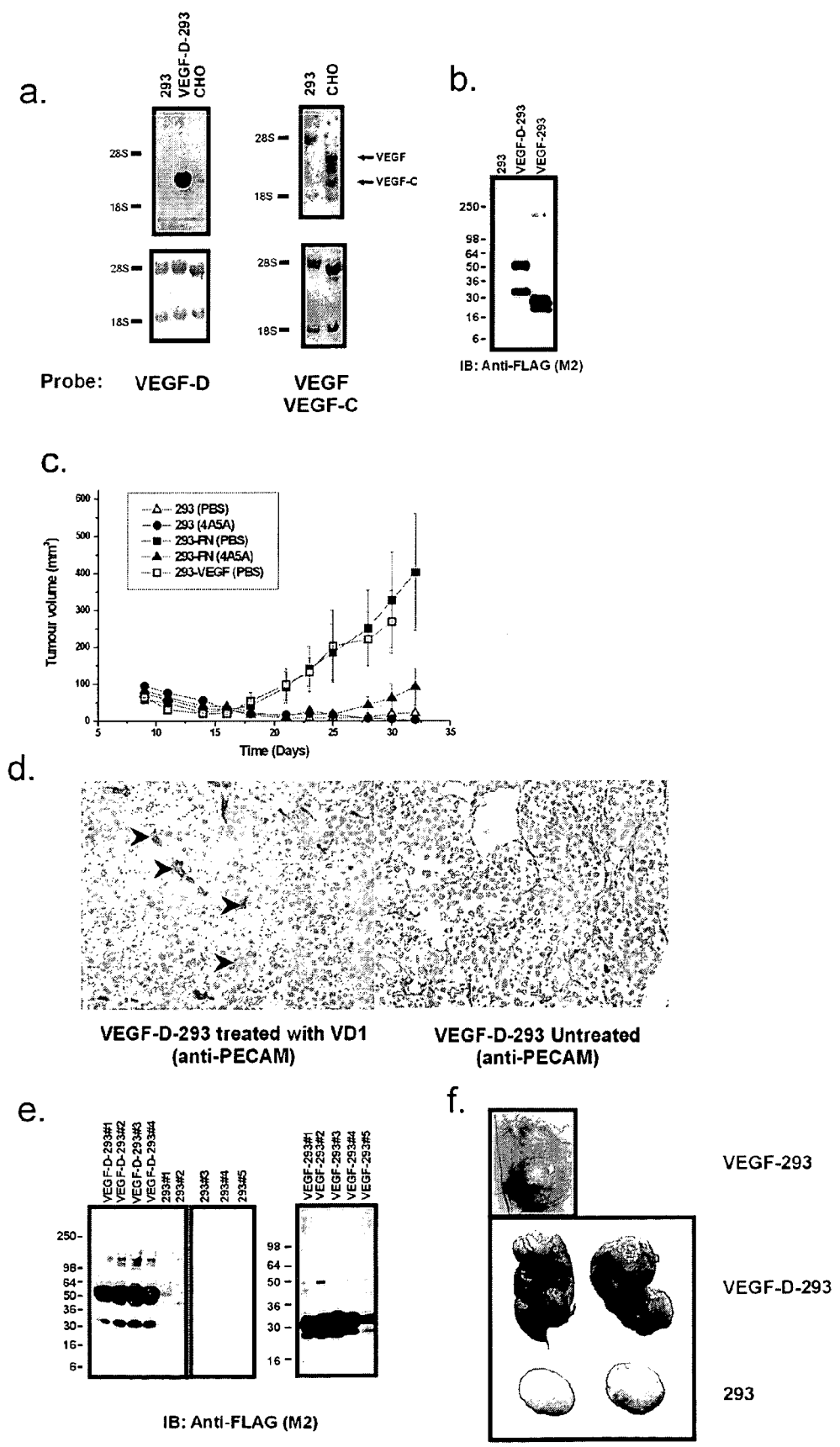
FIGS. 11A-11F show
A lack of detectable levels of VEGF, VEGF-C and VEGF-D in non-transfected 293EBNA cells,
B production of mature forms of the active growth factors in conditioned media from transfected 293EBNA cells,
C growth rate curves for VEGF-293, VEGF-D-293 and control 293 cells,
D distinction between VEGF-D-293 cells with and without growth inhibition through twice weekly doses of Mab VD1 (4A5A),
E analysis for expression of the mature form of the active growth factors from tumors, and
F high vascularization and edema seen in VEGF based tumors, high vascularization only seen in VEGF-D-293 tumors as compared to control 293 tumors.

VEGF-293 cells produced tumors with an increased growth rate compared with control 293 cells, see FIG. 11C. The VEGF-293 tumors were highly vascularized with extensive edema, consistent with VEGF being a potent tumor angiogenesis factor and an inducer of vascular permeability. VEGF-D-293 cells also showed enhanced growth in vivo and the tumors were highly vascularized compared with control 293 tumors but showed no evidence, overtly or microscopically, of edema, see FIG. 11F.

Tumor growth arising from injection of VEGF-D-293 cells was blocked by twice weekly intraperitoneal injections of monoclonal antibody VD1, an antibody specific for the bioactive region of VEGF-D that blocks binding of VEGF-D to VEGFR-2 and VEGFR-3. However, tumor growth was unaffected by treatment with a control, isotype-matched antibody, see FIG. 11D.

Treatment with the VD1 antibody reduced the abundance of vessels in the tumors as assessed by immunohistochemistry for the endothelial cell marker PECAM-1. Western blotting demonstrated the expression of VEGF-D and VEGF in VEGF-D-293 (not shown) and VEGF-293 tumors, respectively, and also that VEGF was not upregulated in VEGF-D-293 tumors, see FIG. 11E. Analysis of tumor weights post mortem demonstrated a significant difference between the VEGF-D-293 tumors (0.49±0.22 g, n=7; mean±SD) and the control 293 tumors (0.123±0.118 g, n=9, p=0.01).

Figure 12:
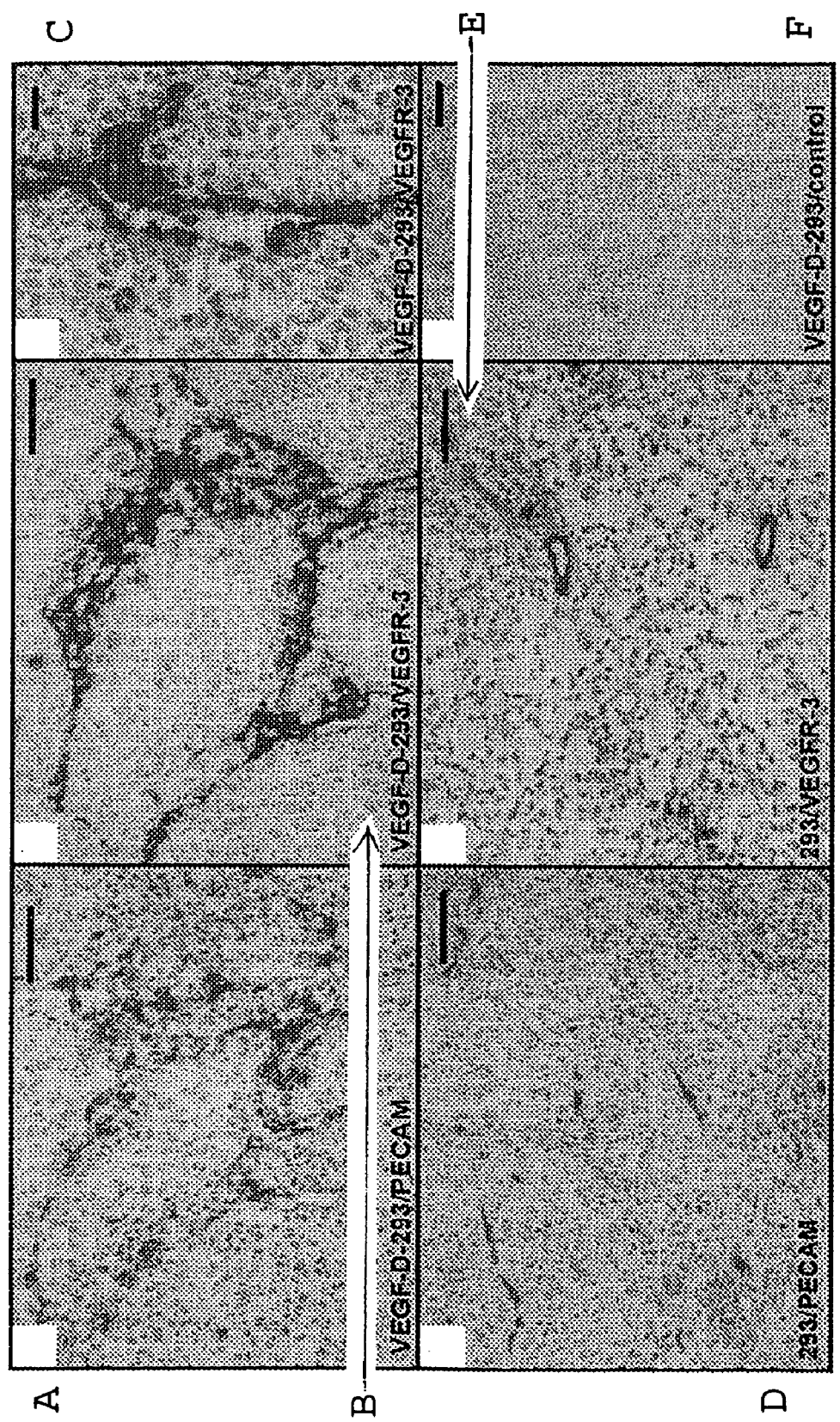
FIGS. 12A-12F show immunohistochemical analysis of tumors with vessels stained for endothelial cell markers PECAM-1 and VEGFR-3.

Gross histological analysis of the VEGF-D-293 tumors showed that they were a solid mass of tumor cells with a characteristic epithelioid like appearance. Immunohistochemical analysis of the tumors showed that vessels within the tumor mass stained for the endothelial cell marker PECAM-1, see FIG. 12A. Comparison of the vessel density of VEGF-D-293 with 293 tumors (FIG. 12D) showed a 3-fold increase in the number of PECAM+ vessels present in the VEGF-D-293 tumors.

Many of these vessels were clearly blood vessels as they contained erythrocytes. Some vessels were large and also expressed VEGFR-2 and VEGFR-3, see FIGS. 12B-12C. VEGFR-3 is expressed predominately on lymphatic endothelial cells in normal adult tissues but can be upregulated on the endothelium of tumor blood vessels. These results indicate that VEGF-D can act as a tumor angiogenesis factor and promote the growth of tumors in vivo, as well as that VEGF-D antagonist antibodies can inhibit tumor growth.

EXAMPLE 11

VEGF-D Induction of Tumor Lymphangiogenesis

Because metastasis to local lymph nodes via the lymphatic vessels is a common step in the spread of solid tumors, experiments were conducted to determine if VEGF-D induced tumor lymphangiogenesis, or if expression of VEGF-D in tumor cells led to spread of the tumor to lymph nodes.

Figure 13:
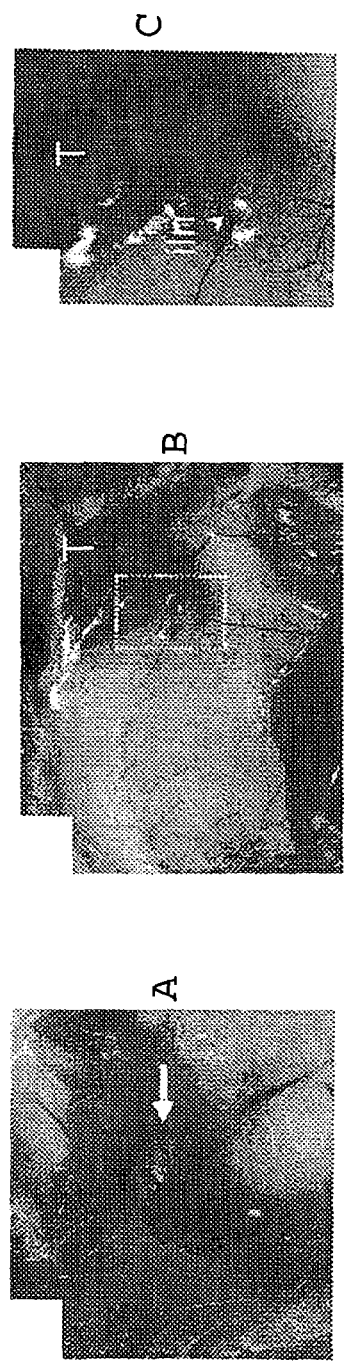
FIGS. 13A-13I show lymph node morphology and histology.

To analyze the role of VEGF-D in tumor spread, VEGF-D-293 tumors were induced in SCID/NOD mice (Animal Resources Center, Canning Vale, Australia; Austin Research Institute, Australia; and Walter and Eliza Hall Institute for Medical Research, Australia). Post-mortem analysis revealed that animals with VEGF-D-293 tumors had developed metastatic lesions in either the lateral axillary lymph node (see FIG. 13A) and/or superficial inguinal nodes (see FIG. 13B-13C) in 14 of 23 animals compared with 0 of 16 animals for VEGF-293 tumors and 0 of 14 animals for 293 tumors. In some cases, the spread of metastatic tumor cells from the primary tumor in SCID/NOD mice was evident as a trail of tumor cells in the lymphatics of the skin between the primary tumors and the lateral axillary node, see FIGS. 13D-13E. Upon histological analysis, these thin walled vessels were found to contain tumor cells, see FIG. 13F.

Injecting patent blue dye, a compound that enters lymphatics but not blood vessels, into the tumor demonstrated that the vessels containing the tumor deposits were lymphatic in nature. Histological analysis of the lymph nodes from VEGF-D-293 tumor bearing animals showed a massive tumor infiltrate within the lymph node, see FIG. 13G. The tumor infiltrate strongly expressed the LYVE-1 and VEGFR-3 markers (see FIGS. 14H-14I), indicating the presence of vessels with lymphatic characteristics, and active lymphangiogenesis Treatment of mice harboring VEGF-D-293 tumors with the VD1 monoclonal antibody (Table 1) blocked the metastatic spread to lymph nodes. None of the 7 mice treated over 25 days with VD1 exhibited lymphatic spread, whereas 6 of 10 mice treated with a control isotype-matched monoclonal antibody exhibited lymphatic spread. These results indicate that VEGF-D can promote the metastatic spread of these tumors via the lymphatics, and that VEGF-D antagonist antibodies can inhibit tumor metastasis.

TABLE 1

Metastatic spread of tumors in SCID/NOC mice

| Tumor line | Number of mice with primary tumors | Number of mice with spread to local lymph nodes |
| --- | --- | --- |
| APEX-293 | 14 | 0 |
| VEGF-293 | 16 | 0 |
| VEGF-D-293 | 23 | 14 (61%) |
| VEGF-D-293 (VD1-treated)[a] | 7 | 0 |
| VEGF-D-293 (LMM774-treated)[b] | 10 | 6 (60%) |

[a]Purified monoclonal antibodies were injected twice weekly over the course of the experiment, starting 1 day after injection of the tumor cells. VD1 is a neutralizing monoclonal antibody against VEGF-D.
[b]LMM774 is an isotype-matched control monoclonal antibody that does not bind VEGF-D.

The data show that expression of VEGF-D can promote metastatic spread of tumor cells through the lymphatic network. VEGF-D induced formation of lymphatic vessels in the tumors, as detected by immunohistochemistry for the lymphatic-specific marker LYVE-1, presumably through the lymphatic receptor VEGFR-3, although activation of VEGFR-3-VEGFR-2-heterodimers cannot be excluded. The expression of lymphangiogenic factors alone is sufficient to induce the formation of lymphatic vessels in the center of a tumor and to facilitate the metastatic spread to the lymph nodes. VEGF-D was localized to tumor cells and the endothelium of vessels in malignant melanoma, lung and breast cancers, see Examples 4-6.

EXAMPLE 12

Presence and Distribution of VEGF-D Induced Lymphatic Vessels

An antibody directed to mouse LYVE-1, which is expressed exclusively on lymphatic endothelium, was used to determine the presence and distribution of lymphatic vessels within VEGF-D and control tumors. Staining of tumor sections showed that LYVE-1+ cells were restricted to the outer connective tissue capsule surrounding the tumor in control 293 tumors and did not form vessel structures, see FIG. 14A. VEGF-293 tumors also had LYVE-1+ cells in the outer connective tissue capsule and to some extent in the connective tissue stroma that extended between large masses of tumor cells, see FIG. 14B. On rare occasions LYVE-1+ vessel-like structures were formed just outside of the tumor mass in VEGF-293 tumors, but were never observed in the tumor mass.

Figure 14:
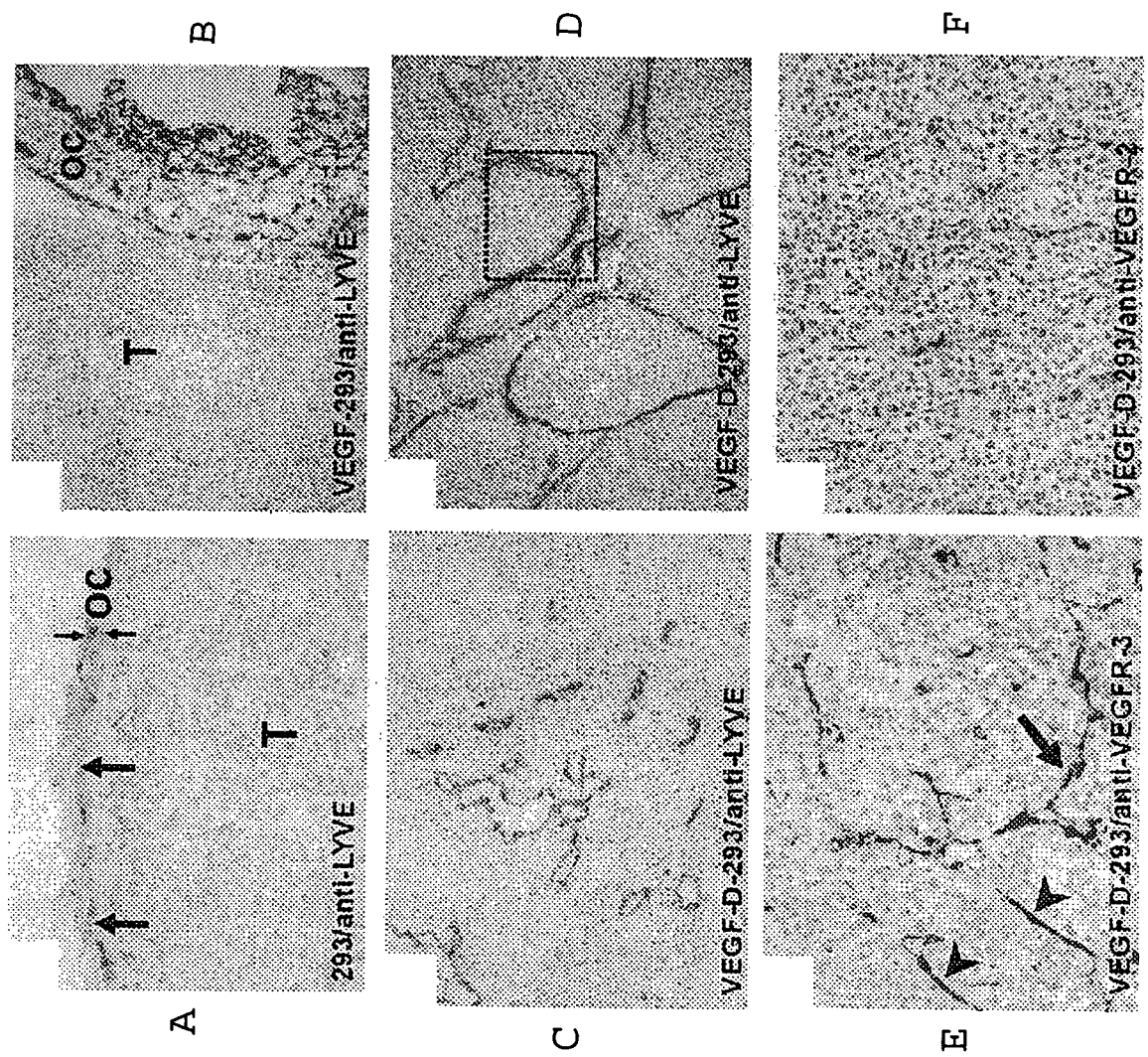
FIGS. 14A-14F show selective staining of tumor sections for LYVE-1+ cells.

In contrast, LYVE-1+ cells in VEGF-D-293 tumors frequently formed into large vessel structures within the tumor mass, see FIGS. 14C-14D. These structures often formed a cluster of vessels in one region of the tumor, although in some cases these vessels were throughout the entire tumor mass. These large LYVE-1+ vessels were, in general, positive for VEGFR-3, see FIG. 14E. However, they were distinct from the blood vessels that were smaller and many of which were positive for VEGFR-3, VEGFR-2 (see FIG. 14F) and PECAM, and negative for LYVE-1.

These results are consistent with a model in which VEGF-D, like VEGF, can drive tumor angiogenesis via VEGFR-2 and thereby support increased growth of 293 cells as tumors in vivo. In addition VEGF-D, but not VEGF, is capable of activating VEGFR-3 and driving lymphangiogenesis. Even though LYVE-1+ cells are present at the periphery of the VEGF tumors it is apparent that expression of VEGF-D is required to signal their growth into the tumor mass and the establishment of lymphatic vessels.

EXAMPLE 13

Variance in Tumor Characteristics Induced by Different Forms of VEGF-D

Figure 15:
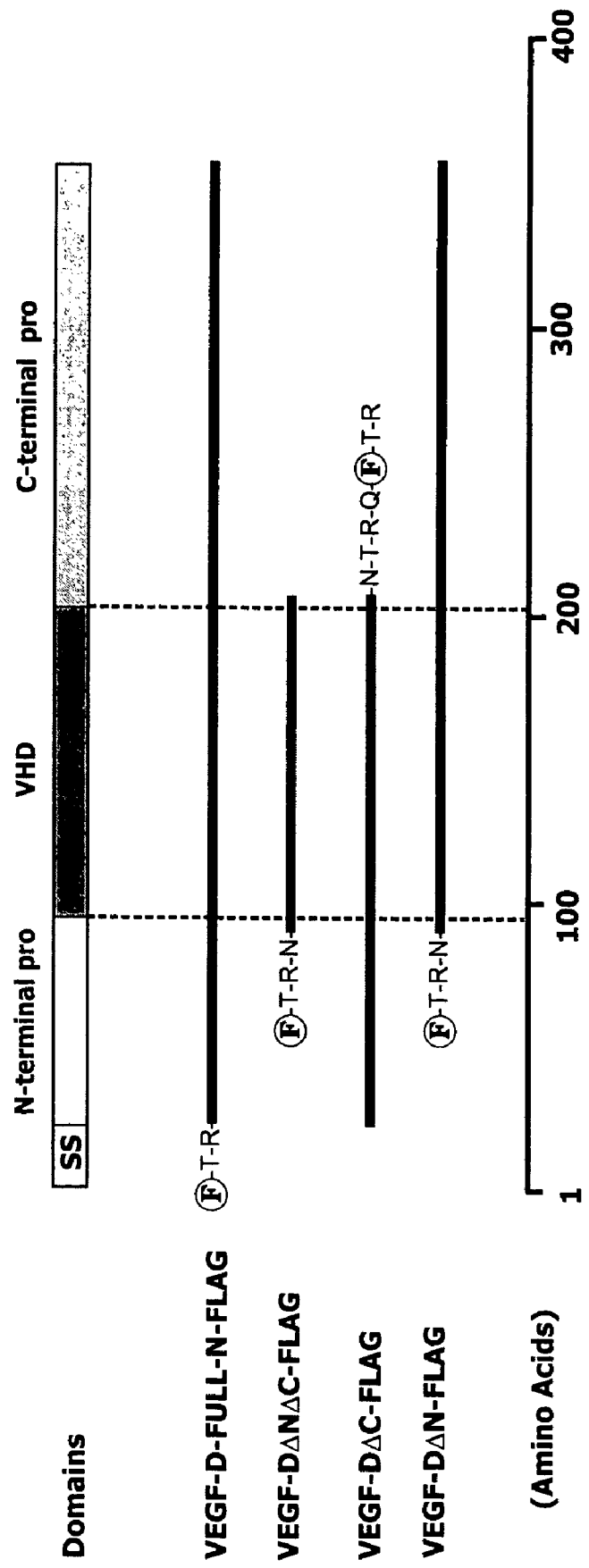
FIG. 15 schematically shows all four domains of full length VEGF-D, as well as the portions of full length VEGF-D present in mutated VEGF-D constructs.

In addition to the determination of the role of VEGF-D in tumor angiogenesis and lymphangiogenesis, tumors expressing different forms of VEGF-D were produced and evaluated. The different forms of VEGF-D represent the cleavage of the N, C, and both N and C terminal propeptides. The regions included in these mutated VEGF-D constructs, as well as reference to the full length VEGF-D, are shown in FIG. 15.

The animals used were six to twenty-one week old female SCID or SCID/nod mice (Animal Resources Centre, Canning Vale, Australia; Austin Research Institute, Australia; Walter and Eliza Hall Institute for Medical Research, Melbourne Australia).

The antibodies used were rat anti-mouse PECAM-1 Mab (Pharmingen, San Diego, CS), a rat anti-mouse Mab raised to the extracellular domain of mouse VEGFR-3 (Kubo, H., et al., Involvement of Vascular Endothelial Growth Factor Receptor-3 in Maintenance of Integrity of Endothelial Cell Lining During Tumor Angiogenesis, *Blood*, 96:546-553, 2000), mouse anti-human VEGF-D Mab VD1 that blocks the binding of VEGF-D to both VEGFR-2 and VEGFR-3 (Achen, M. G., et al., Monoclonal Antibodies to Vascular Endothelial Growth Factor-D Block Interactons with both VEGF Receptor-2 and VEGF Receptor-3, *Eur. J. Biochem.*, 267:2505-2515, 2000), an isotype-matched Mab raised to the receptor for human granulocyte colony-stimulating factor receptor, but non-reactive with mouse G-CSFR, and designated LMM774, M2 (anti-FLAG) Mab (Sigma, St. Louis, Mo.), goat anti-mouse VEGFR-2 polyclonal antibody (R&D Systems, Minneapolis, Minn.), peroxidase-conjugated anti-rat Ig (DAKO Corp., Carpinteria, Calif.), biotin-conjugated anti-rat Ig (DAKO), peroxidase-conjugated anti-mouse Ig (Bio-Rad, Hercules, Calif.), and peroxidase-conjugated anti-rabbit Ig and anti-goat Ig (DAKO).

A tyramide signal amplification (TSA) system (NEN Life Science Products, Boston, Mass.) was used with the biotin conjugated anti-rat Ig for immunohistochemical detection of the VEGFR-3 Mab. Antibody to mouse LYVE-1 was generated in rabbits against a soluble IgFc fusion protein prepared and purified as previously described for the human orthologue (Banerji, S., et al., LYVE-1, A New Homologue of the CD44 Glycoprotein, is a Lymph-Specific Receptor for Hyaluronan, *J. Cell. Biol.*, 144:789-801, 1999). LYVE-1 is a homologue of the CD44 glycoprotein and is a lymphatic-specific receptor for hyaluronan.

Deletion constructs expressing the VHD of VEGF-D with and without the N- and C-terminal domains were prepared to analyze the effects of removal of these regions on VEGF-D polypeptide function. The full length human VEGF-D used was VEGF-D-FULL-N-Flag. It consists of full-length human VEGF-D with an N-terminal FLAG sequence (Stacker, S. A., et al., Biosynthesis of Vascular Endothelial Growth Factor-D involves Proteolytic Processing which generates Non-Covalent Homodimers, *J.Biol.Chem.* 274:32127-32136.16, 1999). Three other constructs were made in which either or both of the N- or C-terminal domains of human VEGF-D were deleted; VEGF-DΔNΔC (Achen, M. G., et al.,. Vascular Endothelial Growth Factor D (VEGF-D) is a Ligand for the Tyrosine Kinases VEGF Receptor 2 (Flk-1) and VEGF Receptor 3 (Flt-4). *Proc.Natl.Acad.Sci.USA* 95:548-553, 1998), VEGF-DΔC and VEGF-DΔN.

VEGF-DΔN is a protein consisting of the VHD and C-terminal propeptide of human VEGF-D tagged at the N-terminus with the FLAG octapeptide. The region of human VEGF-D included in this protein is from residues 93 to 354. Secretion of the protein was ensured by inclusion of the interleukin-3 signal sequence immediately N-terminal to FLAG. Each of these constructs contained a FLAG sequence for isolation. cDNA encoding the full length and mutant VEGF-Ds were subcloned into the expression plasmid APEX-3.

The 293EBNA cell line was stably transfected with the APEX-3 vector alone, or APEX-3 expression constructs for VEGF-D or deletion mutants of VEGF-D. Cell lines were maintained in medium supplemented with 100 µg/ml of hygromycin. The growth rates of the cell lines in vitro were found to be not statistically different when assayed with MTT.

Groups of immunocompromised mice were injected subcutaneously in the mammary fat pads with either 293EBNA, VEGF-D-293, VEGF-DΔNΔC, VEGF-DΔC or VEGF-DΔN cells ($2.0$-$2.5 \times 10^7$) in cell culture medium. The resulting tumors were measured on a regular basis using digital calipers. Animals were sacrificed after three to five weeks and the tumors removed for histological examination. Tumor volumes were calculated using the following equation: volume=length×width$^2$×0.52.

Sections of tumors were immunostained for PECAM-1, VEGFR-2, VEGFR-3 and LYVE-1. Vessels, as defined by staining with anti-PECAM-1 MAb, were counted in 10 randomly selected high-powered fields (×40 magnification) from tumors of each of the test groups (n>5-10). Tumors were excised post mortem on day 25 and weighed. Sections stained with anti-PECAM-1 antibody were assessed for the number of pixels per field which expressed PECAM-1 (Prewett, M., et al., Antivascular Endothelial Growth Factor Receptor (Fetal Liver Kinase 1) Monoclonal Antibody Inhibits Tumor Angiogenesis and Growth of Several Mouse and Human Tumors, Cancer Res. 59:5209-5218, 1999). The density of vascular staining was assessed as the total pixels per field stained for PECAM-1. All statistical analyses were performed using the Mann-Whittney U test (Minitab for Windows, MiniTab Inc.).

Tumor samples and conditioned medium from cell lines in vitro were tested for expression of VEGF-D and VEGF polypeptides. Total cellular RNA was prepared from cell lines and fractionated. Probes used to detect the various forms of VEGF-D were derived from the region of VEGF-D encoding amino acids 163-354 and containing approximately 500 nt of the 3'-untranslated region.

Stable expression of the deletion constructs in 293 cells and analysis of the polypetides secreted into the medium by Western blot demonstrated that the appropriate regions of the VEGF-D polypeptide had been deleted and all could be effectively secreted from the cells. In comparison to VEGF-D-Full-N-FLAG which gave peptides of Mr ~53, ~31 and ~10K by anti-FLAG blotting, VEGF-DΔNΔC produced a 21K species and VEGF-DΔC gave two peptides of ~31 and ~21K respectively. These species were consistent with expectations.

VEGF-DΔN migrated as two species of ~50K and ~21K which represents the VHD alone (21K) and the VHD and C-terminal propeptide (50K), the free C-terminal propeptide, produced when the VHD is cleaved from the propeptide is not detected because it does not have a FLAG tag. VEGF-DΔN was purified to homogeneity by anti-FLAG immunoaffinity chromatography and analyzed in bioassays specific for VEGFR-2 and VEGFR-3. These studies demonstrated that VEGF-DΔN conditioned medium was capable of generating functional ligands for VEGFR-2 and VEGFR-3 as the conditioned medium was able to cross-link these two receptors in the bioassays.

It was observed that the tumors produced by the VEGF-DΔN cells surprisingly grew more rapidly than the tumors produced by control cells. Upon morphological examination the tumors were red in appearance and contained a significant vascular reaction, including a substantial fluid component not seen in the control tumors. The tumors produced by the VEGF-DΔN cells had significant differences in growth and morphological characteristics than the control tumors.

Analysis of VEGF-DΔN purified by anti-FLAG beads showed that the protein did not have the ability to induce premeability on the Miles Assay. When tested in the VEGFR-2 and VEGFR-3 bioassays, however, the VEGF-DΔN material had an approximately ten fold increase in activity towards the VEGFR-2 bioassay. This indicates that the removal of the N-terminal propeptide allows either increased binding to VEGFR-2 or an increased ability to induce dimerization or a conformational change associated with signal transduction.

Figure 16:
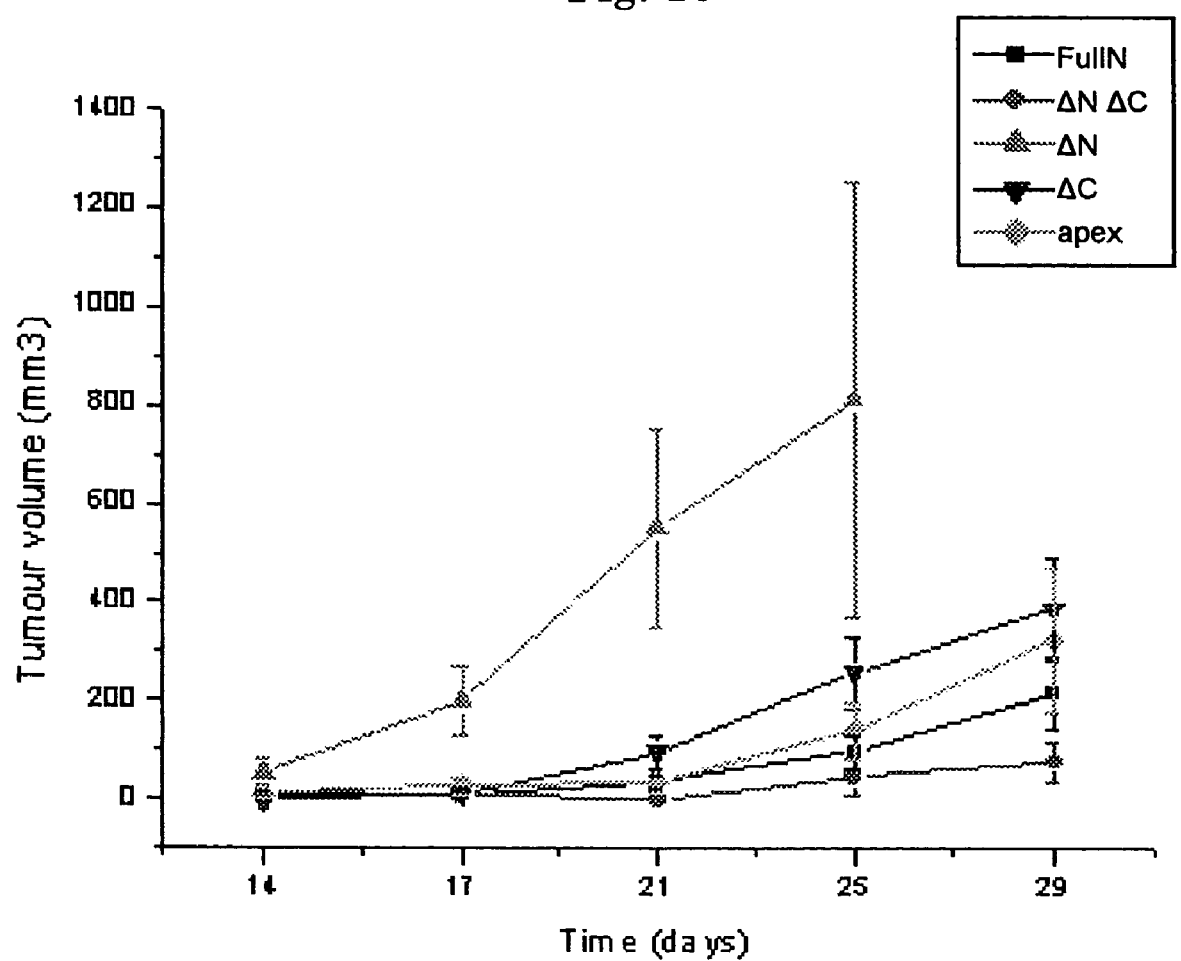
FIG. 16 shows the increased growth rate of VEGF-DΔN-293 tumors.
Figure 17:
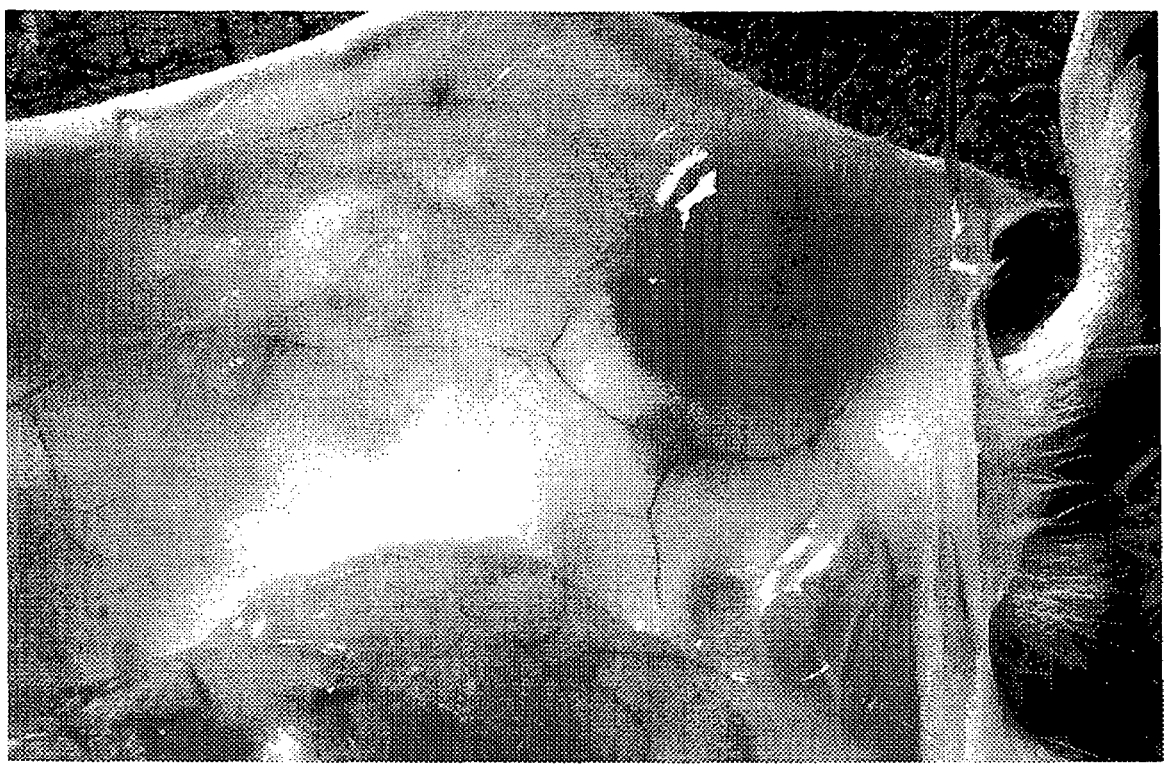
FIG. 17 shows the fluid nature of a VEGF-DΔN-293 tumor.
Figure 18:
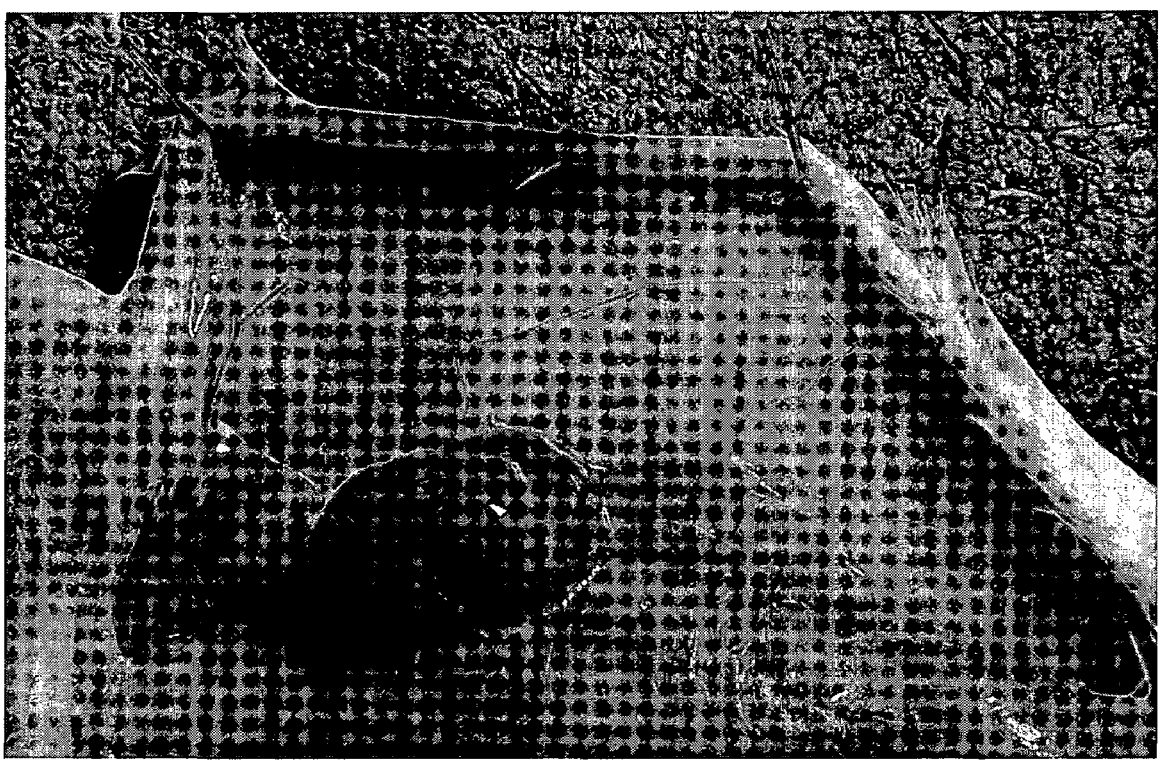
FIG. 18 shows a control tumor.

The graph of FIG. 16 shows the increased rate of growth in tumors from the VEGF-DΔN cells. The tendency toward fluid accumulation in the tumors produced by the VEGF-DΔN cells can be seen in FIG. 17, a photograph of such a tumor. This can be contrasted with the photograph of FIG. 18 which depicts a tumor such as that produced by the control cells.

The tumors produced by the VEGF-DΔC cells grew in a similar fashion to the control cells and did not exhibit excess fluid formation.

Figure 19:
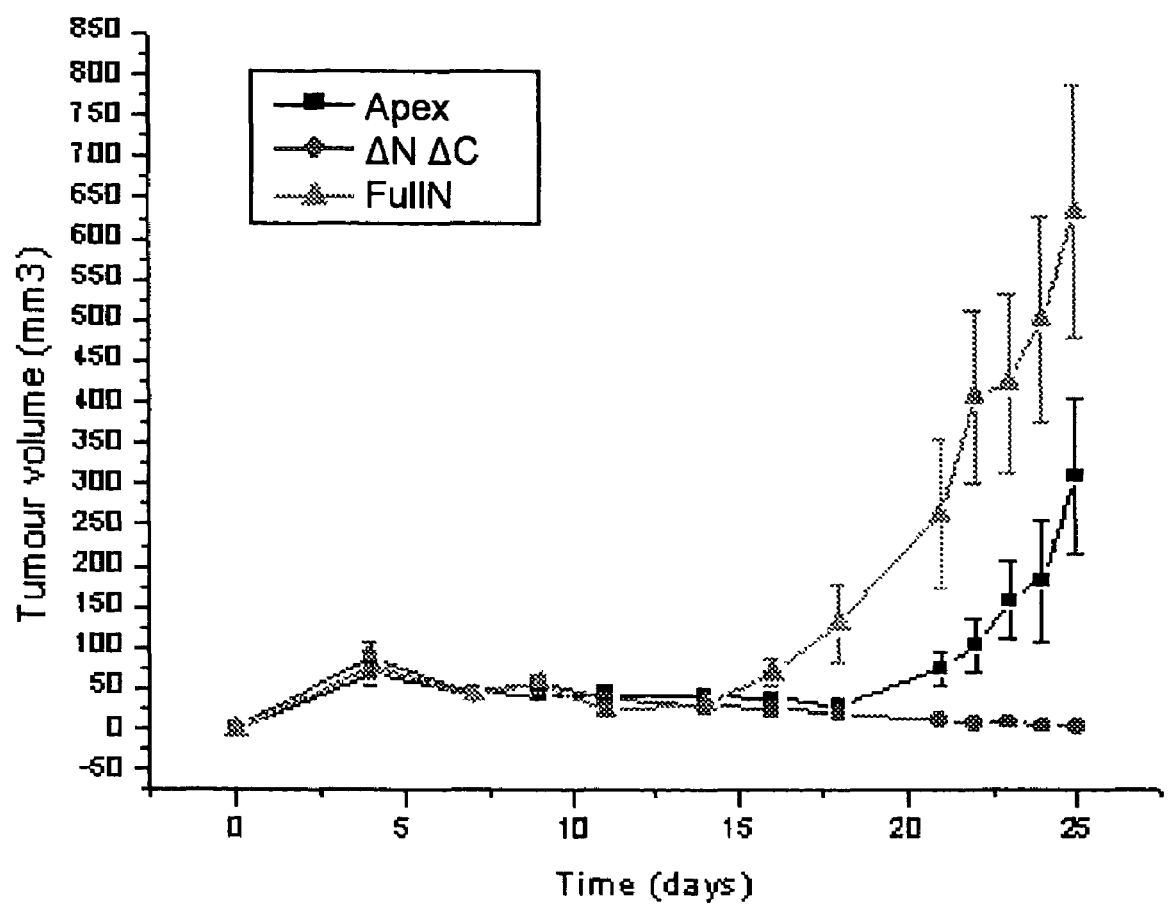
FIG. 19 shows growth curves for 293 tumors, including the slow growth of VEGF-DΔNΔC-293 tumors.
Figure 20:
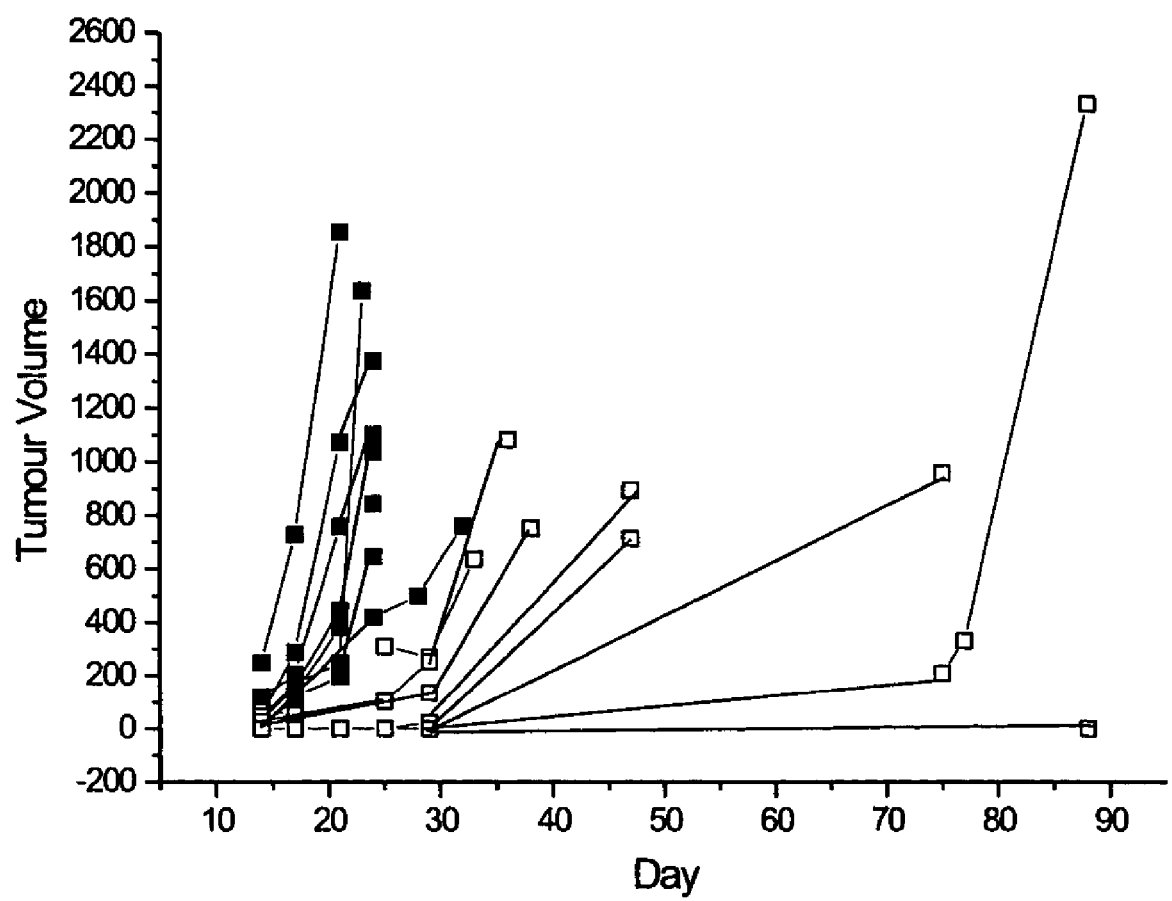
FIG. 20 shows growth curves for VEGF-DΔN-293 tumors and VEGF-DΔNΔC-293 tumors.

The tumors produced by the VEGF-DΔNΔC cells grew very slowly compared to the control tumors. The VEGF-DΔNΔC tumors formed in 40-80 days as compared to an average 30-35 days for the control tumors and 20-25 days for the VEGF-DΔN tumors. Examination of these tumors showed that they had a reduced vascular response, having fewer blood vessels than control tumors by PECAM-1 staining. The tumors developed lymphatic networks as shown by LYVE-1 staining and induced formation of lymphatic metastases. The graph of FIG. 19 shows the decreased rate of growth in tumors from the VEGF-DΔNΔC cells. FIG. 20 shows further growth curve data, depicting the growth of VEGF-DΔN tumors as compared to VEGF-DΔNΔC tumors.

The localization of VEGF-D in malignant melanoma is consistent with a role for this molecule in tumor angiogenesis as strong signals for VEGF-D were detected in the endothelial cells of blood vessels near immunopositive tumor cells, but not in vessels distant from tumor cells. This indicates that VEGF-D found on vessels in or near the tumor may arise due to receptor-mediated uptake, which supports the hypothesis that VEGF-D, secreted by tumor cells, binds and accumulates in target endothelial cells thereby establishing a paracrine mechanism regulating tumor angiogenesis.

A similar pattern of VEGF localization in tumor cells and tumor blood vessels was reported previously (Plate, K. et al., *Brain Pathology* 4: 207-218, 1994). Consistent with the hypothesis that VEGF-D plays a role in tumor angiogenesis is the finding that a receptor for VEGF-D, VEGFR-2, is upregulated in the endothelial cells of blood vessels in tumors (Plate, K. et al., *Cancer Res* 53: 5822-5827, 1993). Indeed, some of the VEGF-D immunopositive vessels detected in the melanomas studied here were also positive for VEGFR-2. Signaling via VEGFR-2 is critical for sustaining tumor angiogenesis (Millauer, B. et al., *Cancer Res* 56: 1615-1620, 1996) and the angiogenic activity of VEGF-D in vivo (Marconcini, L. et al., *Proc Natl Acad Sci USA* 96: 9671-9676, 1999) is most likely mediated by this receptor.

Similar patterns of staining to those seen in the melanomas were observed in squamous cell carcinoma of the lung and breast ductal carcinoma in situ (BDCIS) as VEGF-D was detected in tumor cells and on vessels nearby. Vessels near the tumor-filled ducts in BDCIS and near the islands of tumor cells in lung carcinoma were also positive for VEGFR-2, again suggesting this ligand and receptor may contribute to the control of tumor angiogenesis in a paracrine fashion.

These results also indicate that VEGF-D may play a role in stimulating the growth of lymphatic vessels in the vicinity of malignant melanoma as vessels positive for VEGFR-3, a receptor for VEGF-D expressed on lymphatic endothelium in normal adult tissues, were also positive for VEGF-D. Similar staining patterns were seen in BDCIS as some of the VEGF-D positive vessels surrounding the tumor-filled ducts were also positive for VEGFR-3. Signaling via VEGFR-3 is thought to be important for lymphangiogenesis (Taipale, J. et al., *Curr Top Microbiol Immunol* 237: 85-96, 1999), although this receptor can be up-regulated on blood vessel capillaries in cancer (Valtola, R. et al., *Am. J. Path.* 154: 1381-1390, 1999). Therefore the paracrine regulatory system consisting of VEGF-D and VEGFR-3 could stimulate both lymphangiogenesis and angiogenesis in cancer.

Accordingly, the route by which a tumor metastasizes may be determined, in part, by its capacity to induce angiogenesis and/or lymphangiogenesis. If so, the expression by tumor cells of soluble growth factors which are purely angiogenic (e.g. VEGF) as opposed to those which may also induce lymphangiogenesis (e.g. VEGF-D) could be an important determinant of the route of metastatic spread.

VEGF-D may also play a role in vascular maintenance in non-tumorigenic tissues. In the arterioles of the submucosa of the colon, VEGF-D was localized in vascular smooth muscle, not in the endothelium. The absence of VEGF-D in the endothelium is probably a consequence of the lack of expression of the VEGF-D receptors VEGFR-2 and VEGFR-3 in endothelial cells. Activation of the endothelium in response to vascular damage is probably sufficient to induce expression of VEGFR-2 by endothelial cells (Issa, R. et al., *Lab. Invest.* 79: 417-425, 1999) which would, in turn, render the VEGF-D, produced by vascular smooth muscle, capable of inducing endothelial cell proliferation and thus affecting vessel repair.

These data demonstrate that a novel method for assessing tumor presence is to screen a sample for VEGF-D. Further, detecting the presence of or the elevation of VEGF-D in or around a neoplastic growth indicates likelihood or existence of metastasis of the growth. Screening methods can be employed to better predict disease status and likelihood of disease spread.

In addition to directing new screening methods for neoplastic disease, the present invention also provides treatment methods for neoplastic disease characterized by VEGF-D expression. Antagonists of VEGF-D may be administered to inhibit tumor growth or metastasis.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method of diagnosing growth characteristics of a neoplastic disease in an organism, the method comprising:
   (a) contacting a sample from an organism with a neoplastic disease with an antibody that specifically binds human VEGF-D;
   (b) measuring amount of unprocessed full-length VEGF-D polypeptide having a molecular weight of approximately (~) 53 K in said sample; and
   (c) diagnosing growth characteristics of the neoplastic disease from the amount of the VEGF-D having a molecular weight of approximately (~)53 K measured in step (b), wherein increased unprocessed full-length VEGF-D having a molecular weight of approximately (~)53 K in said sample correlates with increased tumor growth or metastatic risk.

2. The method according to claim 1, wherein said sample is selected from the group consisting of tissue, blood, serum, plasma, urine, ascities fluid and pleural effusion.

3. The method according to claim 2, wherein said sample comprises endothelial cells.

4. The method according to claim 1, wherein said antibody is a monoclonal antibody.

5. The method according to claim 1, wherein said antibody includes a detectable label.

6. The method according to claim 1, wherein said neoplastic disease is selected from the group consisting of malignant melanoma, breast ductal carcinoma, squamous cell carcinoma, prostate cancer and endometrial cancer.

7. The method according to claim 2, wherein said sample is a human tissue sample.

8. The method according to claim 2, wherein said sample comprises a lymph node.

9. A method of diagnosing growth characteristics of a tumor in an organism, the method comprising:
   (a) contacting a tumor sample from the organism with an antibody that specifically binds human VEGF-D;
   (b) measuring amount of unprocessed full-length VEGF-D polypeptide having a molecular weight of approximately (~)53 K in said sample; and
   (c) diagnosing growth characteristics of the neoplastic disease from the amount of the VEGF-D having a molecular weight of approximately (~)53 K measured in step (b), wherein increased unprocessed full-length VEGF-D having a molecular weight of approximately (~)53 K in said sample correlates with increased tumor growth or metastatic risk.

10. The method of claim 9, wherein the antibody is a monoclonal antibody.

11. The method of claim 9, wherein the antibody includes a detectable label.

* * * * *